United States Patent
Wach et al.

(10) Patent No.: US 6,580,935 B1
(45) Date of Patent: Jun. 17, 2003

(54) METHOD AND SYSTEM FOR STABILIZING REFLECTED LIGHT

(75) Inventors: Michael L. Wach, Atlanta, GA (US); Eric T. Marple, Atlanta, GA (US)

(73) Assignee: CIRREX Corp., Atlanta, GA (US)

( * ) Notice: Subject to any disclaimer, the term of this patent is extended or adjusted under 35 U.S.C. 154(b) by 0 days.

(21) Appl. No.: 09/560,590

(22) Filed: Apr. 28, 2000

Related U.S. Application Data

(63) Continuation-in-part of application No. 09/267,258, filed on Mar. 12, 1999, now Pat. No. 6,222,970.
(60) Provisional application No. 60/139,208, filed on Jun. 15, 1999.

(51) Int. Cl.[7] .................................................. A61B 5/00

(52) U.S. Cl. ......................... 600/310; 600/322; 385/115

(58) Field of Search ................................. 600/309–310, 600/322–324, 336, 473, 476; 356/39–42, 300–303; 385/115, 121

(56) References Cited

U.S. PATENT DOCUMENTS

| | | | |
|---|---|---|---|
| 3,187,639 A | 6/1965 | Kelly et al. | ..................... 92/47 |
| 3,761,184 A | 9/1973 | McLaughlin, Jr. | .......... 356/186 |
| 3,796,905 A | 3/1974 | Tomii et al. | ............ 313/92 LF |
| 3,806,256 A | 4/1974 | Ishak | ......................... 356/186 |

(List continued on next page.)

FOREIGN PATENT DOCUMENTS

| | | | |
|---|---|---|---|
| EP | | 185782 A1 | 7/1986 |
| EP | | 210869 A1 | 7/1986 |
| EP | | 237850 A1 | 2/1987 |
| EP | | 286419 A2 | 4/1988 |
| WO | WO 97/34175 A1 | | 9/1997 |
| WO | WO 97/48995 A1 | | 12/1997 |

OTHER PUBLICATIONS

Boiarski Anthony A., "Fiber Optic Particle Concentration Sensor", *SPIE Fiber Optic and Laser Sensors III*, vol. 566, 1985, pp. 122–125.

Bushman, et al., "In Vivo Determination of the Molecular Composition of Artery Wall by Intravascular Raman Spectroscopy," Journal Article submitted by Lileden University Medical Center, et al., published by *Analytical Chemistry*, vol. 72, No. 16, Aug. 15, 2000, pp. 1–14.

Kanda et al., "A New Spherical Mirror–Finish Surface Machining Technology for Optical Fiber Connector", *NEC Res. & Develop.*, vol. 36, No. 2, Apr. 1995, pp. 271–279.

Krohn, David A., "Intensity Modulated Fiber Optic Sensors Overview", *SPIE Fiber Optic and Laser Sensors IV*, vol. 718, 1986, pp. 2–11.

(List continued on next page.)

*Primary Examiner*—Eric F. Winakur
*Assistant Examiner*—Matthew Kremer
(74) *Attorney, Agent, or Firm*—King & Spalding, LLP

(57) ABSTRACT

A light stabilizing interface operatively linked to a collection wave guides for combining and stabilizing reflected light into a substantially even spatial distribution of light energy with a substantially uniform light intensity. The stabilization and substantially even spatial distribution of reflected light can be accomplished by mixing and transmitting device in the form of a single optical fiber and optical junction wave guides in the form of optical fibers having a smaller diameter relative to the mixing and transmitting device. The stabilization and substantially even spatial distribution of reflected light also can be accomplished by a single, integral device that includes a collection wave guide matching section and a transition region. The transition region terminates in a shaped end region that is designed to substantially match the geometry of the input interface of the light processing unit. The method and system for stabilizing reflected light can also enhance the drug development process by providing real-time in-vivo chemical analysis of the interactions between drugs and living tissue.

26 Claims, 6 Drawing Sheets

U.S. PATENT DOCUMENTS

| | | | | |
|---|---|---|---|---|
| 3,874,783 | A | 4/1975 | Cole | 350/96 B |
| 3,906,241 | A | 9/1975 | Thompson | 250/574 |
| 3,910,677 | A | 10/1975 | Becker et al. | 350/196 C |
| 4,191,446 | A | 3/1980 | Arditty et al. | 350/96.15 |
| 4,225,782 | A | 9/1980 | Kuppenheimer, Jr. et al. | 250/216 |
| 4,358,851 | A | 11/1982 | Scifres et al. | 372/97 |
| 4,380,365 | A | 4/1983 | Gross | 350/96.18 |
| 4,449,535 | A | 5/1984 | Renault | 128/634 |
| 4,479,499 | A | 10/1984 | Alfano | 128/665 |
| 4,481,414 | A | 11/1984 | Gasper | 250/226 |
| 4,573,761 | A | 3/1986 | McLachlan et al. | 350/96.24 |
| 4,610,513 | A | 9/1986 | Nishioka et al. | 350/442 |
| 4,615,581 | A | 10/1986 | Morimoto | 350/96.21 |
| 4,654,532 | A | 3/1987 | Hirschfeld | 250/458.1 |
| 4,707,134 | A | 11/1987 | McLachlan et al. | 356/342 |
| 4,732,448 | A | 3/1988 | Goldenberg | 350/96.18 |
| 4,733,933 | A | 3/1988 | Pikulski | 350/96.2 |
| 4,812,003 | A | 3/1989 | Dambach et al. | 350/96.18 |
| 4,816,670 | A | 3/1989 | Kitamura et al. | 250/277 |
| 4,830,460 | A | 5/1989 | Goldenberg | 350/96.26 |
| 4,867,520 | A | 9/1989 | Weidel | 350/96.16 |
| 4,892,388 | A | 1/1990 | Taylor | 350/320 |
| 4,914,284 | A | 4/1990 | Halldorsson et al. | 250/206.2 |
| 4,919,891 | A | 4/1990 | Yafuso et al. | 422/58 |
| 4,930,516 | A | 6/1990 | Alfano et al. | 128/665 |
| 4,957,114 | A | 9/1990 | Zeng et al. | 128/665 |
| 4,958,897 | A | 9/1990 | Yanagawa et al. | 350/96.15 |
| 4,979,797 | A | 12/1990 | Nemeth | 350/96.29 |
| 4,981,138 | A | 1/1991 | Deckelbaum et al. | 128/665 |
| 4,995,691 | A | 2/1991 | Purcell, Jr. | 350/96.15 |
| 5,011,254 | A | 4/1991 | Edwards et al. | 350/96.18 |
| 5,011,279 | A | 4/1991 | Auweter et al. | 356/28.5 |
| 5,037,180 | A | 8/1991 | Stone | 385/123 |
| 5,074,632 | A | 12/1991 | Potter | 385/31 |
| 5,112,127 | A | 5/1992 | Carrabba et al. | 356/301 |
| 5,131,398 | A | 7/1992 | Alfano et al. | 128/665 |
| 5,146,917 | A | 9/1992 | Wagnieres et al. | 128/397 |
| 5,166,756 | A | 11/1992 | McGee et al. | 356/446 |
| 5,196,005 | A | 3/1993 | Doiron et al. | 606/7 |
| 5,253,312 | A | 10/1993 | Payne et al. | 385/31 |
| 5,263,952 | A | 11/1993 | Grace et al. | 606/15 |
| 5,269,777 | A | 12/1993 | Doiron et al. | 606/7 |
| 5,288,992 | A | 2/1994 | Fohl | 250/216 |
| 5,308,656 | A | 5/1994 | Emmons | 427/282 |
| 5,318,023 | A | 6/1994 | Vari et al. | 128/663 |
| 5,330,465 | A | 7/1994 | Doiron et al. | 606/7 |
| 5,348,018 | A | 9/1994 | Alfano et al. | 128/665 |
| 5,377,676 | A | 1/1995 | Vari et al. | 128/634 |
| 5,402,506 | A | 3/1995 | O'Rourke et al. | 382/50 |
| 5,402,508 | A | 3/1995 | O'Rourke et al. | 385/31 |
| 5,404,218 | A | 4/1995 | Nave et al. | 356/301 |
| 5,413,108 | A | 5/1995 | Alfano | 128/665 |
| 5,421,339 | A | 6/1995 | Ramanujam et al. | 128/665 |
| 5,421,928 | A | 6/1995 | Knecht et al. | 156/153 |
| 5,432,880 | A | 7/1995 | Diner | 385/85 |
| 5,456,260 | A | 10/1995 | Kollias et al. | 128/665 |
| 5,460,182 | A | 10/1995 | Goodman et al. | 128/664 |
| 5,467,767 | A | 11/1995 | Alfano et al. | 128/665 |
| 5,474,910 | A | 12/1995 | Alfano | 435/34 |
| 5,482,041 | A | 1/1996 | Wilk et al. | 128/653.1 |
| 5,486,378 | A | 1/1996 | Oestreich et al. | 427/163.2 |
| 5,507,287 | A | 4/1996 | Palcic et al. | 128/633 |
| 5,521,733 | A | 5/1996 | Akiyama et al. | 359/127 |
| 5,529,680 | A | 6/1996 | Kitada et al. | 205/67 |
| 5,579,773 | A | 12/1996 | Vo-Dinh et al. | 128/665 |
| 5,590,660 | A | 1/1997 | MacAulay et al. | 128/664 |
| 5,596,987 | A * | 1/1997 | Chance | 600/310 |
| 5,599,717 | A | 2/1997 | Vo-Dinh | 436/63 |
| 5,604,588 | A * | 2/1997 | Goedert | 356/318 |
| 5,612,540 | A | 3/1997 | Richards-Kortum et al. | 250/461.2 |
| 5,631,986 | A | 5/1997 | Frey et al. | 385/78 |
| 5,636,307 | A | 6/1997 | Cowen et al. | 385/102 |
| 5,647,368 | A | 7/1997 | Zeng et al. | 128/665 |
| 5,652,810 | A | 7/1997 | Tipton et al. | 385/12 |
| 5,660,181 | A | 8/1997 | Ho et al. | 128/665 |
| 5,697,373 | A | 12/1997 | Richards-Kortum et al. | 128/664 |
| 5,699,795 | A | 12/1997 | Richards-Kortum et al. | 128/634 |
| 5,710,626 | A | 1/1998 | O'Rourke et al. | 356/301 |
| 5,764,840 | A | 6/1998 | Wach | 385/123 |
| 5,774,278 | A | 6/1998 | Kaplan | 359/723 |
| 5,835,661 | A | 11/1998 | Tai et al. | 385/146 |
| 5,864,397 | A * | 1/1999 | Vo-Dinh | 356/301 |
| 5,878,178 | A | 3/1999 | Wach | 385/55 |
| 5,901,261 | A | 5/1999 | Wach | 385/38 |
| 5,911,017 | A | 6/1999 | Wach et al. | 385/12 |
| 5,939,137 | A | 8/1999 | Kuck et al. | 427/163.2 |
| 5,953,477 | A | 9/1999 | Wach et al. | 385/115 |
| 5,974,837 | A | 11/1999 | Abbott, III et al. | 65/432 |

OTHER PUBLICATIONS

Ku, R.T., "Progress in Efficient/Reliable Semiconductor Laser–to–Single–Mode Fiber Coupler Development," Jan. 23, 1984, pp. 4–6.

McCann Brian P., "Specialty Optical Fibers Resolve Challenging Application Problems", *Lightwave*, Nov. 1994, pp. 48, 51–52.

Russo V. and Margheri G., "Lens Ended Fiber–Fiber Connections for Power Laser Applications", *SPIE ECOOSA*, vol. 701,1986, pp. 220–225.

Russo et al., "Microlens–Ended Fibers: A New Fabrication Technique", *Insituto di Ricerca sulle Onde Elettromagnetiche, Firenze, Italy*, pp. 21–27.

Shintaku et al., "Highly Stable Physical–Contact Optical Fiber Connectors with Spherical Convex Ends", *Journal of Lightwave Technology*, vol. 11, No. 2, Feb. 1993, pp. 241–248.

Shintaku et al., "Connection Mechanism of Physical–Contact Optical Fiber Connectors with Spherical Convex Polished Ends", *Applied Optics*, vol. 30, No. 36, 1991, pp. 5260–5265.

Tan W. et al., "Submicrometer Intracellular Chemical Optical Fiber Sensors", *Science*, vol. 258, Oct. 30, 1992, pp. 778–781.

* cited by examiner

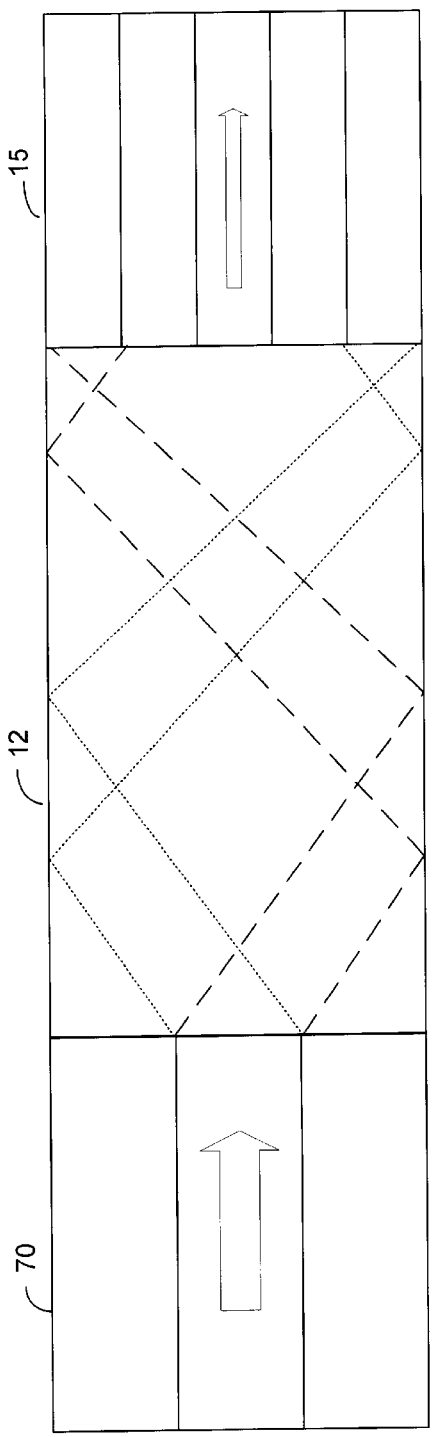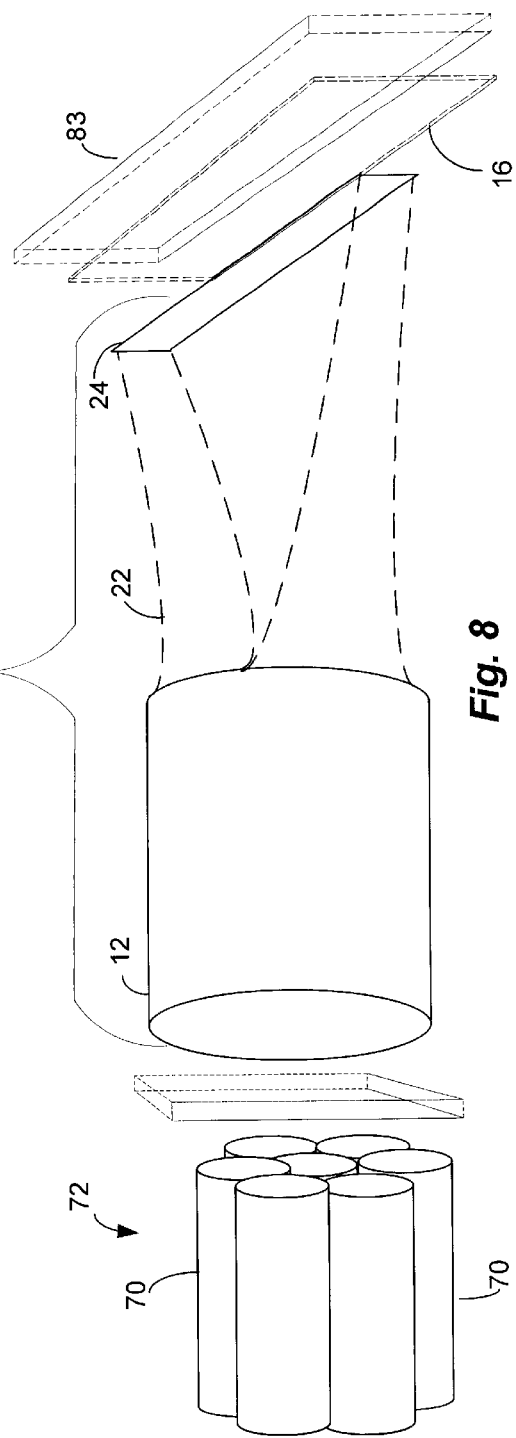

METHOD AND SYSTEM FOR STABILIZING
REFLECTED LIGHT

STATEMENT REGARDING RELATED
APPLICATIONS

This application is a continuation in part of U.S. patent application Ser. No. 09/267,258, now U.S. Pat. No. 6,222, 970, entitled "Method and Apparatus for Filtering an Optical Fiber," filed Mar. 12, 1999, and claims benefit of priority to U.S. Provisional Application No. 60/139,208, entitled, "Enhanced Methods and Systems and for In Vivo Analysis by Light-Based Characterization with High Specificity," filed Jun. 15, 1999, the entire contents of the provisional and non-provisional applications are hereby incorporated by reference.

TECHNICAL FIELD

This invention relates generally to the manipulation of light carried by optical fibers. More particularly, the present invention relates to stabilizing reflected light propagating along optical fibers.

BACKGROUND OF THE INVENTION

In recent years, the use of optical fibers has become increasingly widespread in a variety of applications. Optical fiber probes have been found to be especially useful for analyzing materials by employing various types of light-scattering spectroscopy.

Optical fibers offer numerous advantages over other types of source/detection equipment. In short, the fiber provides a light conduit so that the source-generating hardware and the recording apparatus are stationed independently of the subject under investigation and the point of analysis. Thus, analyses are conducted remotely in otherwise inaccessible locations. Previously unattainable information is acquired in situ, often in real-time. This capability is sought in numerous industrial, environmental, and biomedical applications. The laboratory is moved on line in the industrial realm, to the field in the environmental sector, and in vivo in the biotechnical arena. Additionally, hardware and measurements are more robust, quicker, less intrusive, more rugged, less costly, and many other advantages are realized.

Light Scattering Spectroscopy

While transmission spectroscopy analyzes light passing through a substance, lights-scattering spectroscopy entails illumination of a measurand and analyzing light that is scattered at angles relative to the incident source. The photon-matter interactions of the scattering events may be either elastic or inelastic. In an inelastic event, a photon's energy (wavelength) changes as a result of the light-matter interaction. In an elastic event, a photon's energy (wavelength) does not change. Absorption, the phenomena in which a fraction of photons are entirely absorbed, also plays a role in light-scattering spectroscopies. Raman, diffuse, reflectance, and fluorescence spectroscopies are of particular interest as they relate to vibrational and nonvibrational photonic responses of a material.

The Raman effect describes a subtle light-matter interaction. Minute fractions of light illuminating a substance are Raman-scattered in random directions. Raman-scattered light is color shifted from the incident beam (usually a laser). The color (frequency) shifts are highly specific as they relate to molecular bond vibrations inducing molecular polarizability changes. Raman spectroscopy is a powerful technique for chemical analysis and monitoring. The resulting low light levels require sophisticated, expensive instrumentation and technical complexity. Suitable technology and products for on-line analysis of processes and environmental contaminants are just becoming available.

Specular reflectance relates to a surface's mirror-like aspects. Diffuse reflectance relates to light that is elastically scattered from a surface of material at diffuse angles relative to the incident team. For example, a projector screen diffusely reflects light while a glossy, new waxed car has a high specular component. Diffuse reflectance spectroscopy is important for chemical analysis as well as measuring visual perception. Among other things, it is based on particulate-scattering and absorption events.

Fluorescence relates to substances which absorb light at one wavelength then re-emit it at a longer wavelength as a result of electronic transitions. As an example, a "highlighter" felt-tip marker appears to "glow" green as it absorbs blue and ultraviolet light then emits it as green. Fluorescence provides a powerful technique for chemical monitoring.

Raman spectroscopy is a well-established laboratory technique and is generally recognized as having enormous potential for on-line monitoring and sensing. With the advent of stable lasers, cheap computing power, efficient detectors, and other new technological advancements, Raman spectroscopy is primed for widespread industrial monitoring deployment. In addition to process control monitoring, it will be utilized in specialized monitoring and sensing devices ranging from neuroimaging to environmental monitoring, to in vitro and in vivo medical testing.

Raman spectroscopy involves energizing a sample with a high-power, narrow-wavelength energy source, such as a laser. The laser photons induce low intensity light emissions as wavelengths shift from the laser's. The Raman effect is an elastic scattering of photons The emitted Raman light is collected and analyzed with a specialized instrument.

The spectral positions (colors) of the shifts provide fingerprints of the chemicals in the sample. Thus, Raman spectroscopy provides a means for chemical identification. The intensity of the shift (the spectral peak height) correlates to chemical concentration. Thus, a properly calibrated instrument provides chemical content and concentration. In practicality, Raman spectroscopy is technically complex and requires sophisticated, expensive instrumentation.

Raman spectroscopy is well suited to aqueous-based media without sample preparation. From this standpoint, it is an ideal tool for process control medical testing and environmental applications. Thus, Raman spectroscopy has great potential for real-time monitoring and is being vigorously pursued.

The basic concept for a probe-based, on-line Raman instrument is simple. Laser light is directed down an optical fiber to a remote probe. The laser light exits the fiber and illuminates the sample medium. Another fiber picks up the Raman-emitted light and returns it to the instrument for analysis.

In practicality, the engineering challenges for a robust physical probe implementation are substantial. In addition to the optical performance expected by laboratory instruments, a probe must be hardened to withstand extreme physical and chemical conditions. Optical characteristics must also remain constant as dynamic conditions change.

Optical aspects of probe engineering require particular design finesse. The Raman effect involves very weak signals. Raman emissions may be one trillionth as intense as the exciting radiation. Subsequently, the probe must be incredibly efficient in collecting and transmitting Raman-emitted light. And, the signal must not be corrupted by extraneous influences. As an example of the sensitivity, Raman instruments typically feature cosmic ray filters. The mechanisms identify and discard measurement data samples influenced by passage of a single cosmic ray photon through the detector.

A phenomenon known as the silica-Raman effect has proven especially troublesome for those engaged in remote Raman spectroscopy. As laser light is transmitted over optical fibers, a subtle light-matter interaction inherently occurs. The laser light and the silica in the glass fiber interact generating "silica-Raman" light. The extraneous silica-Raman light becomes wave guided in the fiber and hopelessly mixed with the laser light. The purity of the laser light is corrupted. Fiber fluorescence causes similar problems.

Remote Raman spectroscopy employs optical fiber between the base instrument and the remote probe or process interface. Optical fiber delivers laser light from its source to the probe. Separate fiber returns sensed light from the probe to an instrument for analysis. In both delivery and return, undesirable silica-Raman light travels in the fibers concurrently with desirable laser and sensor light. A major obstacle in fiber-optic-based Raman spectroscopy has been in separating the desirable light from the undesirable silica-Raman light.

In addition to the undesirable Silica-Raman light, another problem exists with the separate fiber or fibers that return reflected light from the probe to the instrument for analysis. Specifically, problems arise when dispersive instruments are used to analyze the collected reflected light. Various light processing units or instruments require specific fiber input configurations. While non-dispersive light instruments typically accept light input via optical wave guides having a circular geometry, dispersive light instruments or light processing units typically perform best when the input or optical wave guide is shaped into a narrow rectangle. Such an input configuration is often referred to as a slit. This slit geometry makes it difficult to provide collection wave guides that can readily adapt to a specific configuration without degrading the quality and quantity of the collected reflected light energy.

Further, for the configurations in which ring fibers are employed to collect light, the light from these fibers can vary in intensity from one fiber to another due to either imperfections along individual fibers or due to relative different intensities at the actual collection site on a sample. Many dispersive light processing units or instruments, such as spectrographs, require the collected reflected light at the slit input to be of a substantially even intensity in order to enhance the analysis of the reflected light.

Accordingly, a need in the art exists for a method and system for stabilizing reflected light that is fed into a dispersive light processing unit, such as a spectrograph. There is a further need in the art for a method and system for stabilizing reflected light in addition to properly shaping the collected light wave guides to substantially match the input geometry configuration of a light processing unit.

Drug Development and the Long Felt Need for in-vivo Chemical Analysis

Drug development starts with the compilation of a list of candidate compounds. These may be derived from any number of methods ranging from extracts of natural products to automated development and design techniques. Combinatorial chemistry is one of these techniques. Currently, the technique is very time consuming. A need in the art exists for a method and system that can enhance the drug development process through real-time in vivo chemical analysis which, in turn, will decrease the amount of time for tracking the effects that drugs have on organisms. But to better appreciate this need for in-vivo chemical analysis, a discussion of the current state of drug development is necessary.

Drug Development Through Combinatorial Chemistry

Combinatorial chemistry is the synthesis of large numbers of compounds that are systematic variants of a chemical structure. Traditionally, searching for new chemicals meant assembling molecules one at a time in individual test tubes. Over decades, shelves of created compounds have been generated and collected and later are screened again, one at a time, against a molecular target; it is a tedious process. Combinatorial chemistry shifts compound design from a one-molecule-at-a-time approach to automated parallel synthesis. Starting with a useful compound or molecule, robotics may be used to spin a lead into hundreds of thousands of chemical variations. The resulting chemical diversity boosts the chance that a new compound will usefully react with a molecular target.

In the last 15 years, combinatorial chemistry has expanded from peptides to organic, organometallic, inorganic and polymer chemistry. Industrial applications not only include pharmaceuticals but also electronic materials; catalysts; polymers; pigments for plastics, coatings and fabrics; advanced materials; and agricultural chemicals. The initial mechanism of drug action is the specific binding or docking of a portion of the drug candidate to a receptor site. This action is conceptually similar to that of many catalysts in promoting chemical reactions, particularly polymerizations. So, it is not surprising that combinatorial chemistry is being used to synthesize catalyst candidates. Similarities also exist between material science and drug discovery. The properties of materials are not always predictable from the structures, and synthesis is complex. Material scientists and researchers need better ways to manage arrays of materials and identify chemical properties of interest.

Using the combinatorial chemistry technique, one typically begins with a molecule or compound known to be useful. The substance is separated into labeled fragments, often anchoring the pieces to a solid support (e.g., polystyrene beads). Then, using automation, a variety of other molecular fragments are added. This parallel processing quickly produces a vast collection of chemicals that are then stored. By screening the library against a drug target, one can assay any compound or molecule that reacts with a disease target.

Two different combinatorial approaches may be used to generate a large number of compounds for high throughput screening; they are the 1) mix-and-split synthesis approach; and 2) parallel synthesis approach.

Mix-And-Split Synthesis Approach of Combinatorial Chemistry for Drug Development In the "mix-and-split synthesis" approach, compounds are simultaneously created and then the mixture is screened for performance. Reactions occur in the solid phase. The compounds are synthesized on polystyrene beads allowing for very large libraries to be made in a short time. Each bead holds a different pure compound, and each reaction vessel has a mixture of many compounds on separate beads. After a reaction, the beads are split into separate containers, and different agents are added. The beads containing the products of these reactions are mixed then split again and reacted with different reagents. The process is repeated a certain number of times. If activity is found then the compound on the beads causing the activity must be determined. Tags attached to the beads at each step indicate the reagents with which each bead has been treated. After the synthesis is complete, the beads are screened for performance. The chemical structure of the most active compound in the mixture is identified, and this compound is prepared using standard synthetic methods. It is re-synthesized in measurable quantities, purified and then tested. This combinatorial method is best suited for the synthesis of many (up to one million) compounds called a library. The attraction of this combinatorial approach is the speed and cost effectiveness of generating molecular diversity. The challenge is to develop methods to readily identify the active component in a complex mixture either through labeling or statistical methods.

Parallel-Synthesis Approach of Combinatorial Chemistry for Drug Development

In the "parallel synthesis" approach, all chemical structure combinations are separately prepared, in parallel, on a given chemical structure (scaffold) using an automated robotic synthesis apparatus. Thousands of vials may be used to perform these reactions, and laboratory robots are programmed to deliver specific reagents to each vial. Although this approach is automated, it often takes longer than the mix-and-split synthesis approach to complete and thus is best suited for the development of smaller chemical libraries.

Biotechnology, pharmaceutical and chemical companies are applying combinatorial chemistry and high throughput synthesis techniques to change the field of chemistry as applied to drug discovery. For drug developers, combinatorial chemistry offers great advantages. It enables a dramatic reduction in development time (four to seven years) by speeding up the synthesis and the identification of lead compounds. In today's economy, drug competition is heightened by both the agenda set by the present managed-care climate and the drive for inexpensive drugs that become the top choice of healthcare buyers. So, companies are scrambling to create entirely new pharmaceuticals.

At the same time, the Human Genome Project and other gene-hunting efforts are producing DNA sequences for disease-related enzymes and cell receptors. Many of these molecules will ultimately generate successful drugs as chemicals are synthesized that control them. The combinatorial approach is a significant advancement in finding such chemicals-applying the principles of parallel processing to medicinal chemistry.

The introduction of high throughput screening methods in the pharmaceutical industry in the early 1990s produced a fundamental mismatch of skill sets. Medicinal chemists were unable to generate compounds at a pace that fully utilized the capacity of high throughput screening. Today, however, with molecular modeling and combinatorial chemistry, the capacity of high throughput screening is better used. Molecular modeling provides 1) new hypotheses of the mode of drug action, and 2) the identification of key chemical structure features that drug candidates must have. Combinatorial chemistry enables candidate molecules with both desired and ancillary chemical structure features to be rapidly synthesized. And, with combinatorial chemistry the number of molecules that can be made and tested far exceeds the capacity of most high throughput screening.

The drug development process may utilize combinatorial chemistry to create libraries biased towards compounds with desirable properties, such as solubility or a low molecular weight. Such properties make drugs easier for the human body to accept and use. The winning product may come as a complete surprise. At times, a diverse library with as many as 15,000 components is made, out of which a reasonable candidate is selected, then analogs of the candidate are made to find "the winner."

With combinatorial chemistry and high throughput synthesis, a 10- to 50-fold annual increase in the number of compounds made and tested can be realized. Existing information technologies and business operations, such as compound registration practices and assay result visualization, cannot accommodate this increase. Traditional chemical registration systems may be used for registering discrete compounds associated with the synthetic effort; information systems for the registration and storage of combinatorial chemistry products may also be used. However, it is more popular (but less desirable) to store assay results and related library information within relational databases (e.g., "Oracle" database) or when no central storage of assay data is available, then the information is saved within desktop programs (e.g., "Excel" spreadsheet program). In addition to registration, tracking the synthesis, testing, and heritage of deconvolution products is important.

Synthesis direction includes: 1) combinatorial mixes only, 2) high throughput synthesis only, 3) emphasis on combinatorial mixtures, but high throughput synthesis is pursued, and 4) emphasis on high throughput synthesis, but combinatorial mixtures are pursued.

The intent of combinatorial chemistry efforts includes: 1) lead generation, 2) lead optimization, and 3) combinatorial mixtures for lead generation and high throughput synthesis for lead optimization. Combinatorial chemistry is not exclusively used for lead generation. Other synthetic efforts include: 1) the use of known solution phase chemistry, 2) the use of solid phase chemistry (e.g., peptides, peptoids), and 3) the development of solid phase organic synthesis (SPOS) for novel, non-oligomeric compounds.

From a list of candidate compounds, the compounds are tested for their effects on organisms. Ultimately, the best candidate compounds are tested on humans. However, there is a high failure rate associated with this animal/vertebrate/human testing and it is very time consuming.

Conventional Experimental Clinical Drug Trials

Experimental drugs are administered in clinical trials in attempts to assess their efficacy on a disease, disease state, affliction, ailment, or health/medical condition. Along with a control, the drug is administered to a group of people/animals. An assessment is made as to the drug's efficacy by observing the disease's progression or regression. In some instances this observation is straightforward, but typically it has not been. Furthermore, the observation and assessment has been outcome based which adds to the time for analysis.

For example, a clinical research study may be organized to assess the efficacy of a baldness remedy. The test remedy, for instance a pill that is ingested, may be selected from a group of candidate treatments thought likely to be effective. The test remedy may be administered to a group along with a control group receiving a placebo. Periodically, haircounts are taken on the members of the test study. The remedy's effectiveness is determined by changes in the hair count. Consequently, outcome assessment is not difficult. However, the study provides minimal information on the mechanisms of treatment. Suppose the outcome concluded that the test remedy was effective in 10% of the group. Did only the 10% have elevated levels of the ingested chemical in their scalp? If so, maybe a better drug delivery system is needed. Did 100% exhibit sufficiently elevated levels of the chemical in their scalp but only 10% possess a naturally occurring biochemical that is known to be easily regulated pharmacologically? If so, maybe 100% success could have been achieved by artificially bolstering the biochemical. The described outcome-based approach provides no direct answers to these questions.

In light of the above, there is a need in the art for a method and system that can enhance the drug development process through real-time in vivo chemical analysis which, in turn, will decrease the amount of time for tracking the effects that drugs have on organisms. A further need exists in the art to ascertain, in real-time, the presence and quantity of applied chemicals on living tissue.

Therefore, a need in the art exists for a method and system for stabilizing reflected light that is fed into a dispersive light processing unit such that real-time in vivo chemical analysis can be provided. An additional need in the art exists for a method and system for stabilizing reflected light that facilitates accurate and rapid tracking of effects that drugs have on organisms.

SUMMARY OF THE INVENTION

The present invention solves the problems of collected reflected light for instruments by providing a light stabilizing interface linked to a collection wave guides for combining and stabilizing reflected light into a substantially even spatial distribution of light energy with a substantially uniform light intensity. Even spatial distribution and uniform intensity of reflected light energy are desirable qualities and enhance light measurement techniques such as Ramon spectroscopy.

The stabilization and substantially even spatial distribution of reflected light can be accomplished by a mixing and transmitting device comprising a single optical fiber and optical junction wave guides in the form of optical fibers having a smaller diameter relative to the mixing and transmitting device. The optical junction wave guides are shaped into a linear array in order to maximize the light fed into an input interface of a light processing unit that has a predefined geometrical configuration (usually a slit). The junction wave guides enhance the coupling between the collection wave guides and light processing unit by increasing the spatial resolution of the light energy propagating therethrough. Further, the junction optical waveguides can be sized such that the numerical aperture of the linear array is optimally matched to the light acceptance characteristics of the light processing unit. The light processing unit can be a "fast" spectrograph that accepts high numerical aperture fibers, which in turn, increases light processing efficiency.

For another aspect of the present invention, the stabilization and substantially even spatial distribution of reflected light can be accomplished by a single, integral device that includes a collection wave guide matching section and a transition region. The transition region terminates in a shaped end region that is designed to substantially match the geometry of the input interface of the light processing unit. For example, the shaped end region can have a substantially rectangular shape to match to the substantially rectangular shape of the input interface. The total surface area of the transition region can be designed to remain constant relative to the collection wave guide matching section. The light stabilizing interface can substantially reduce light energy loss due to the reduced number of interfaces between the collection waveguides and light processing unit.

In another aspect of the present invention, a method and system for stabilizing reflected light can enhance the drug development process by providing real-time in-vivo chemical analysis of the interactions between drugs and living tissue. This supports an accurate detection of chemical composition and quantity in living tissue. This real-time chemical detection is possible with a light management system of the present invention that can be inserted into or adjacent to an organism.

That the present invention improves over the drawbacks of the prior art and accomplishes the objects of the invention will become apparent from the detailed description of the illustrative embodiments to follow.

BRIEF DESCRIPTION OF THE DRAWINGS

FIG. 7 illustrates ray tracing for light beams emanating from collection wave guides passing through the light stabilizing interface shown in FIG. 4.

FIG. 8 is a diagram that illustrates a light stabilizing interface according to an alternate exemplary embodiment of the present invention.

DETAILED DESCRIPTION OF EXEMPLARY EMBODIMENTS

Figure 1:
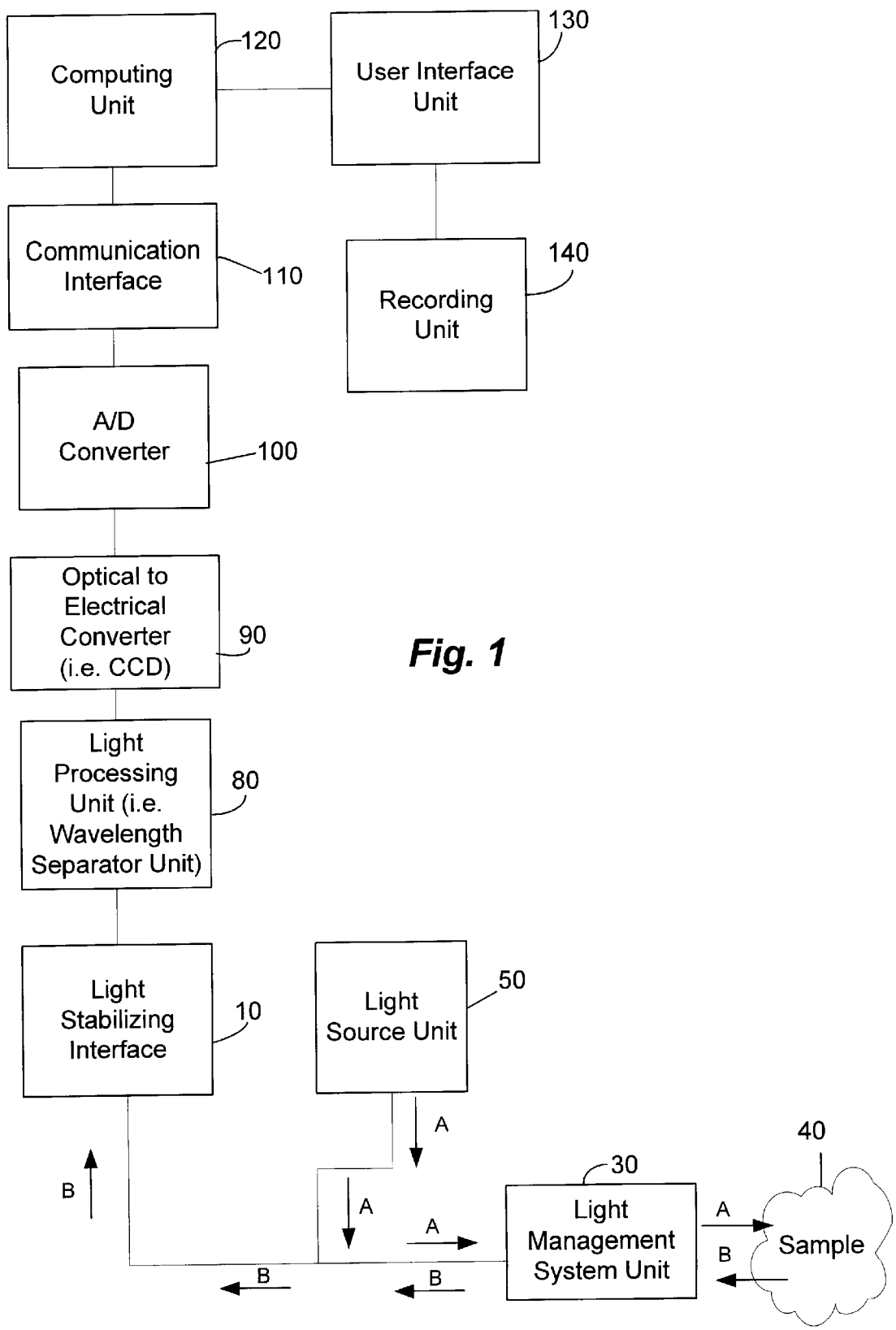
FIG. 1 is a functional block diagram of a system for stabilizing and shaping reflected light in accordance with an exemplary embodiment of the present invention.

An inventive fiber-optic probe disposed in a light management system can provide selective sensitivity for capturing disproportionate responses associated with specific light matter interactions. Light manipulation techniques are applied internal to the fiber in order to allow the illumination and collection zones to be altered for specific light matter interactions. Probe performance is enhanced by applying filters to fiber segments, isolating the fibers that form the probe tip, and fusing the fibers together to make them as close as possible.

An exemplary embodiment of the present invention includes fiber optic probes that employ the "GASER" light management system developed and marketed by the assignee of the present application, Visionex, Inc. of Atlanta, Ga. This system incorporates a number of novel fiber optic light manipulation and management methods which are described in U.S. Pat. No. 5,953,477 issued to Wach et al., the content of which is hereby incorporated by reference. Each of these light manipulation and management methods is useful for diverse fiber optic applications spanning from telecommunications to high power laser delivery.

A Review of Optical Fibers in General

The term "optical fiber" is used herein to refer generally to any optical wave guide or structure having the ability to transmit the flow of radiant energy along a path parallel to its axis and to contain the energy within or adjacent to its surface. "Step index," "gradient index," and "single mode" fibers are subcategories within the optical fiber designation. The term "multimode" optical fiber refers to an optical wave guide that will allow more than one bound mode to propagate.

Step index fibers include a transparent cylindrical core of relatively high refractive index light-conducting material. Typical core materials include silica, plastic, and glass. The core is cylindrically surrounded by a medium having a lower refractive index. Typically, this medium is a relatively thin cladding, which is an intimately bound layer surrounding the core. The cladding may be a different material than the core, or it may be a similar material that has been doped in order to reduce its refractive index. The core may also be unclad whereby the ambient medium, often air, is of lower refractive index and acts in the capacity of the cladding. The cladding is usually surrounded by one or more coatings, buffers, and/or jackets that primarily serve protective roles.

An arbitrarily oriented ray within the core of a step index fiber travels until it intersects the core boundary at the cladding and interacts in accordance with its angle of incidence. Generally, rays angularly oriented close to parallel with the fibers axis are efficiently reflected at the core boundary. Within certain angular limitations, the ray is oriented to undergo total internal reflection at the core interface. These angular limitations are a function of the refractive indices of the core and the cladding. The limits determine the angular bounds within which the fiber can propagate light. Thus, sustained propagation occurs via repeated total internal reflection within the fiber core. If the arbitrary ray is oriented beyond the fiber's limits for total internal reflection, then only a fraction of its intensity is internally reflected. The reduced intensity ray is further attenuated as it undergoes subsequent core boundary interactions. The ratio of light energy that is internally reflected to the energy that escapes varies according to the angle. If the ray is oriented normal to the core boundary, then all of its intensity is lost. As the angle of an improperly oriented ray approaches the acceptance limits for total internal reflection, the relative intensity of the reflected ray increases. Thus, for rays with angle orientation close to, but outside of, the limits for total internal reflection, multiple reflections can occur prior to significant power loss.

If the arbitrarily oriented ray within the fiber core has sufficient power and orientation, then it sustains power and eventually reaches the fiber end face. It interacts with the end face boundary in accordance with the laws of reflection and refraction. As the ray crosses the end face boundary between the fiber's core and the surrounding medium, it is refracted. The refractive effect is a function of the refractive index of the core, the refractive index of the surrounding medium, and the orientation of the ray relative to the fiber end face surface. The factor of ray orientation is based upon its angle relative to a surface normal taken at the point where the ray intersects with the end face surface boundary. Angular orientation of rays outside the fiber end face and propagating rays within the fiber core are distinctly correlated. Thereby, a correlation exists between individual and collective external and internal rays.

The previous discussion centered on rays internally propagating and exiting the fiber. An analogous situation exists for rays outside the optical fiber entering into the fiber core. The correlating development is readily drawn by those skilled in the art. For a fiber utilized for single-direction flow of light, light is typically injected into the fiber at one end and exits the fiber at the opposite end. However, fibers can also be utilized in a bidirectional configuration. In this configuration, light purposely enters and exits from a single end of the fiber.

As light propagates within the fiber core, it tends to become mixed or randomly oriented over distance. Even highly directional sources, such as lasers, become mixed or scrambled over distance following input into a long optical fiber. In this mixing process, the fiber's modes are filled and all source characteristics, or so-called launch conditions, are lost. The mixing process can be accomplished in shorter fibers by tightly coiling the fiber, inducing micro-bends, or otherwise stressing the fiber. Similarly, for very short fiber lengths, launch characteristics are retained. Also, for very short lengths of fiber, light can be transmitted beyond the normal limits for propagation dictated by the angular limits for total internal reflection. This property is due to the reduced number of reflections, which accumulate minimal attenuation. A fiber's ability to sustain transmission beyond the normal limits for total internal reflection can be enhanced by the application of internally reflective coatings applied to the fiber's outer cylindrical surface. This coating can be applied to either the fiber's core or the cladding. It should be noted that for long fibers, propagation cannot be totally reliant on reflective coatings. In contrast to total internal reflection, even the best reflective coatings offer less than 100 percent reflectivity. Losses associated with repeated reflections at less than 100 percent efficiency quickly accumulate resulting in severe attenuation. Vast numbers of reflections occur during propagation in even moderate fiber lengths.

FIG. 1 illustrates an exemplary operating environment for a light stabilizing interface 10. The light stabilizing interface 10 is part of a Raman spectroscopy system 20. The Raman spectroscopy system 20 includes a light management system unit 30 that irradiates a sample 40. The light management system unit 30 typically includes "GASER" based probes which are disclosed in U.S. Pat. No. 5,953,477 to Wach et al. A light source unit 50 is linked to the light management system unit 30 by one or more optical feed wave guides 60. In addition to the light source unit 50, the light management system unit 30 is also linked to the light stabilizing interface 10 by one or more collection wave guides 70. The light stabilizing interface 10 is further linked to a light processing unit 80.

During operation, the light source unit 50 generates light that flows through optical feed wave guides 60 in directions denoted by arrows labeled A. The light generated by the light source unit flows through the light management system unit 30 and is directed to the sample 40. The sample 40 reflects the light energy back to the light management system unit 30 in a direction according to the arrows labeled B. The reflected light travels along the collection wave guide(s)70 to the light stabilizing interface 10. The light stabilizing interface 10 can manipulate the light and feeds it to the light processing unit 80.

The light processing unit 80, typically a dispersive instrument such as a spectrograph, feeds the light energy to an optical-to-electrical converter 90, such as a charged-coupled device (CCD). The optical-to-electrical converter 90 then passes the converted energy to an analog-to-digital (A/D) converter 100. The A/D converter 100 is linked to a communication interface 110. It is noted that the term "link" used herein between hardware elements can include many different types of connections. Other types of connections or "links" include, but are not limited to, cables, wires, optical fibers, or wireless means, such as by RF devices or infrared transmitting/receiving devices.

The communication interface 110 links a computing unit 120 to the A/D converter 100. Although, the computing unit 120 is typically implemented by a personal computer, it will be understood that other computing units, such as hardwired systems, are not beyond the scope of the present invention. The computing unit 120 is linked to a user interface unit 130 that typically includes a display screen. The user interface unit 130 is also linked to a recording unit 140 such as a storage medium. The storage medium can be either volatile or non-volatile. While the computing unit 120, user interface unit 130, and recording unit 140 are illustrated as separate units, one of ordinary skill in the art recognizes that these units can be part of an integrally-formed, general purpose computer.

The components illustrated in FIG. 1 provide an exemplary system designed for light scattering spectroscopy that involves measuring and analyzing light that is scattered at angles relative to an incident light source. The light scattering spectroscopy system 20 is well-suited for the application of Raman spectroscopy. However, other fiber optic applications for the light stabilizing interface 10 are not beyond the scope of the present invention. Other fiber optic applications include, but are not limited to, telecommunications, high-powered laser delivery, and other similar types of applications.

Figure 2:
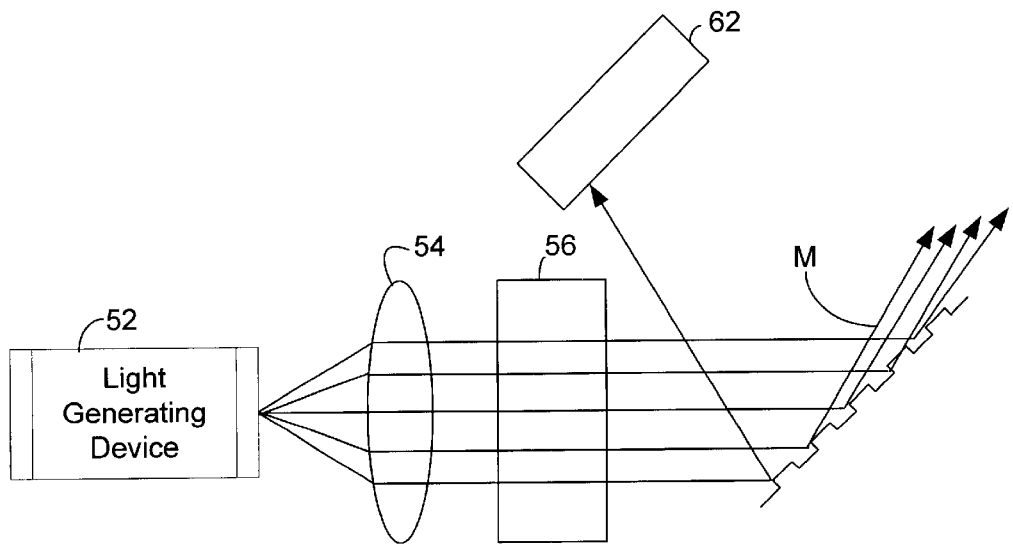
FIG. 2 is a functional block diagram illustrating an exemplary light source unit for the system diagram of FIG. 1.

FIG. 2 illustrates an exemplary embodiment of the light source unit 50. The light source unit 50 typically includes a light generating device 52 such as a lasing diode. The light generating device 52 is typically a high-power laser that delivers approximately 100 milliwatts to 300 milliwatts of power to a sample, such as living tissue, over a 200$\mu$ (micrometer)-diameter circle. The light generating device 52 can operate at a wave length of 830 nanometers or greater to minimize fluorescence. An exemplary description of an external cavity stabilized diodide laser is presented by Gavrilovic et al. in an article entitled, *Narrow-Lined Width Operation of a Broad-Stripe Single Quantum Well Laser Diode in a Quizzing Incidents External Cavity*, Applied Physics Letters, Vol. 60, No. 24, Jun. 15, 1992. Vendors that sell lasers stabilized and suitable for this type of application include SDL of San Jose of Calif. and Process Instruments of Salt Lake City, Utah.

The exemplary light generating device 52 produces light that is stable and has a constant wave length. Typically, when external feedback lasers are used as the light generating device 52, the light produced has high purity and is monochromatic. To produce this highly pure and monochromatic light, the light generating device 52 directs light towards a colliminating lens 54 that passes the light energy through a zero-order half-wave plate 56. The light is then directed towards a grating 58 where the light is reflected toward a mirror 62. The mirror 62 then reflects the light back to the grating 58, which results in the propagation of monochromatic light M from the laser generating device 50. The reflected light originating from the mirror 62 will allow the laser generating device 50 to lock onto light of a particular wavelength such that the ouput of the light generating device 50 remains constant.

The highly monochromatic and constant wavelength laser light M is launched into the proximal end of an optical feed wave guide 60 (depicted schematically in FIG. 1). The highly monochromatic laser light M then propagates from the optical feed wave guide 60 into the light management system unit 30. FIG. 2 illustrates an exemplary embodiment of the light management system unit 30.

Referring now to FIG. 2, the light management system unit 30 provides light segregation functionality to prevent the source light or monochromatic light M and the sample-reflected light R from commingling with one another which, in turn, prevents interference or noise. Disposed between the first beam steering mechanism 36A and the second beam steering mechanism 36B is a cross-talk minimizer 35. The cross-talk minimizer 35 can include a metalization layer that is part of a respective fiber's outer sidewalls in areas not requiring through-the-wall light transmission. Similarly, an opaque foil can be utilized as the cross-talk minimizer 35 to block cross-talk between the first beam-steering mechanism 36A and second beam-steering mechanism 36B.

In the light management system unit 30, the monochromatic light M propagates along an optical feed wave guide 32 and passes through a monochromatic enhancer that minimizes the interference effects of the optical feed wave guide 32. The monochromatic enhancer 34, which is typically a band-pass filter, passes the monochromatic light M with only minimal transmission of the interference light. The off-wave length and undesirable interference light is reflected off and away from the monochromatic enhancer 34.

The interference light typically degrades the wavelength purity of the propagating monochromatic laser light M due to light-matter interactions with the optical wave guide's fiber materials which produce wavelength-shifted light. This "silica-Raman" interference light is due to Raman scattering and fiber fluorescence; it is not specific to silica materials. The propagation characteristics of a fiber accumulates this extraneous light, which can interfere with material analysis techniques, such as fiber-optic-based laser-Raman spectroscopy. Interfering light can also arise from other sources, such as laser instability (mode hopping) and ambient light sources entering the pathway.

After the monochromatic light M passes through the monochromatic enhancer 34, it propagates through the first beam-steering mechanism 36A. The beam-steering mechanism 36A delivers the monochromatic light M into the sample 40. After the monochromatic light M has interacted with the sample 40, the reflected and inelastically scattered or wave length-shifted light R is then collected by a second beam steering mechanism 36B. The first and second beam-steering mechanisms 36A, 36B are typically reflectors, but other beam steering mechanisms are not beyond the scope of the present invention. Other beam steering mechanisms include, but are not limited to, lenses, highly refractive index materials such as sapphire coated with low index fluoropolymers, filters, and other like beam steering mechanisms.

The collected reflected light R is directed towards a source light blocker 38. The collected reflected light R has a spectral composition which includes the laser wavelength and shifted wavelengths. The source light blocker 38 is typically a high-wavelength pass filter that blocks returning laser light and permits Stokes-shift Raman light to pass therethrough. If returning laser light was permitted to pass, such returning laser light would generate Silica-Raman interference. The source light blocker 38 can also be a band stop (notch) filter exhibiting high quality filtering characteristics.

Both the monochromatic enhancer 34 and the light source blocker 38 in the exemplary embodiments exhibit minimum ripple and a high-packing density above 90%. In other embodiments, the packing density for each of these devices can be above 95%. In further embodiments, the packing density can be above 99%. The monochromatic light M in an exemplary embodiment is distally filtered to at least an optical density of 2, and, in other exemplary embodiments, to a value of 3 or 4. The return collected light R is preferably filtered similarly to the monochromatic emitted light M. The light source blocker 38 is preferably able to transmit at least from 800–2000 centimeters$^{-1}$ Raman-shifted light. After passing through the source light blocker 38, the reflected collected light R continues propagating along a collection wave guide 70.

Figure 4:
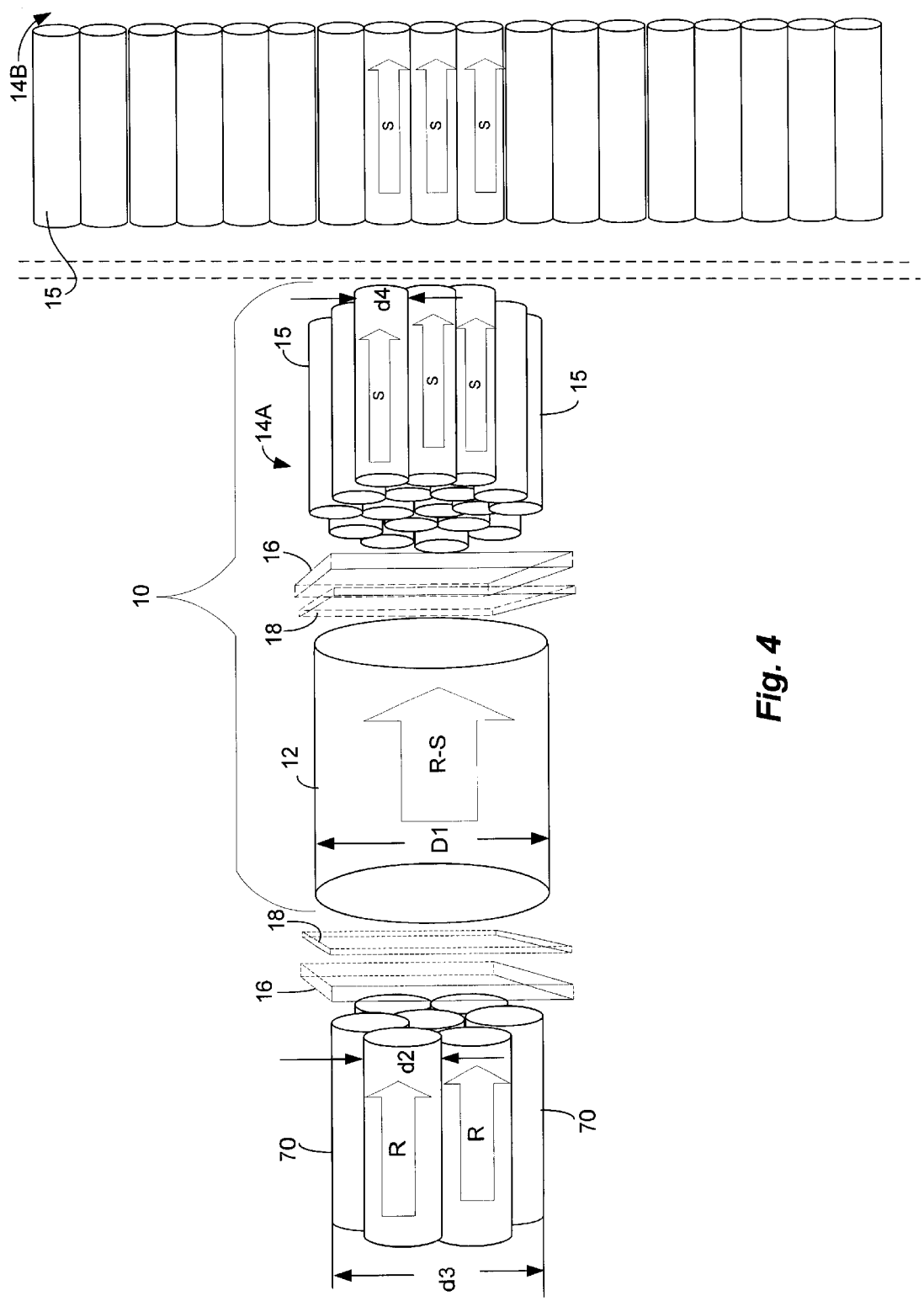
FIG. 4 is a diagram that illustrates a light stabilizing interface according to an exemplary embodiment of the present invention.

FIG. 4 illustrates a first embodiment of the light stabilizing interface 10. The reflected light R propagates along the collection wave guides 70 forming a collection wave guide bundle 72 and is fed into a mixing and transmitting device 12 of the light stabilizing interface 10. The mixing and transmitting device 12 is typically a large-core optical fiber. An exemplary optical fiber is silica core/silica clad with a coating such as polyamide, which strips cladding modes. In the embodiment illustrated in FIG. 4, the mixing and transmitting device 12 has a diameter D1 while the collection wave guides 70 each have diameters d2. Diamter D1 is preferably greater than each diameter d2 of the individual collection wave guide 70. Further, diameter D1 is also greater than diameter d3 of the collection fiber bundle 72 formed by the collection feed wave guides 70. Since the mixing and transmitting device 12 has a diameter D1 that is slightly larger than the diameter d3 of the collection wave guide bundle 72, the mixing and transmitting device 12 overcomes the effect of divergence if the reflected light R spreads during transmission from the collection wave guide bundle 72 to the mixing and transmitting device 12.

The mixing and transmitting device 12 combines the light propagating along the individual collection wave guides 70. By combining the collected reflected light R, the mixing and transmitting device 12 stabilizes the intensity of the reflected light R in a substantially even or uniform manner. This stabilizing function is desirable because the reflected light entering an individual collection wave guide at a probe tip (such as reflecting region 36B of FIG. 3) may have a different intensity relative to reflected light R entering another collection wave guide 70. To improve spectroscopic analysis, the light entering a spectrograph preferably exhibits an even intensity to facilitate rapid and accurate processing of the collected light. Although light density decreases as a result of the change from multiple fibers to a single fiber, the total light energy of reflected light R is not significantly decreased. This effect typically does not decrease the performance of the light processing unit 80.

The combined and stabilized collected light R-S is then fed into a plurality of junction fibers 15 that form a substantially circular junction fiber bundle 14. The junction fiber bundle 14 as well as the collection wave guides bundle 72 are formed by fusing individual wave guides together so that each bundle has maximum efficiency where there are no gaps between the fibers. A filter 16 can be placed at the interface between the mixing and transmitting device 12 and the collection wave guides 70. Alternatively, a filter 16 can be placed at the interface between the mixing and transmitting device 12 and the junction wave guides forming the fiber bundle 14. Additionally, filters (not shown) could be placed on the individual junction fibers 15 of the fiber bundle 14. In another implementation (not shown), thin-film filters can be applied to wafers that are placed between the mixing and transmitting device 12 and each junction wave guide 15. The filter 16 is typically an interference-type filter having a packing density of at least 95%, and in another embodiment greater than 99%. The filter 16 minimizes the air interfaces between the mixing and transmitting device 12 and the respective fiber bundles 72 and 14.

The filter 16 may include alternating layers of high/low refractive index materials or may be implemented as rugate interference filters that are applied directly to the wave guide. Instead of applying the filters directly to an end face of a wave guide, in other embodiments, filter wafers may be utilized. For example, the filter 16 may be applied onto a thin wafer which is situated within a coupling between two wave guide end faces. The wafer may be attached to one of the fiber end faces prior to assembly or inserted as a separate unit.

Filter performance requirements for demanding applications, such as Raman spectroscopy, typically include: a) high throughput in transmission wavelength region; b) high-attenuation (dense) blocking in rejection wavelength regions; c) steep transition between wavelength regions of rejection and transmission; d) environmental stability; e) low ripple in passage regions, f) minimal sensitivity to temperature variation; g) no performance fluctuation with ambient humidity or chemicals; h) the ability to withstand high, and rapidly changing, temperatures present in sterilization processes and industrial processes; i) physical toughness; and j) tenacious adhesion between filter and substrate.

To couple each respective fiber bundle 72 and 14 to the mixing and transmitting device 12, an optical matching gel or optically transparent epoxy/cement 18 can be used to increase coupling efficiency. The matching gel or transparent epoxy/cement 18 is typically a refractive index matching substance that is used to couple optical signals into or out of optical wave guides. Such products can be purchased from Thor Labs, Inc. of (Newton, N.J.,). The matching gel or transparent epoxy/cement 18 can come in a variety of phases, such as a gel, liquid, or resin.

To match the input of the light processing unit 80, the fiber bundle 14 is shaped similarly to the mixing and transmitting device 12 on a first end 14A. On a second opposing end 14B, the fiber bundle 14 is shaped into an appropriate configuration for the input aperture 83 of the light processing unit 80. In the embodiment illustrated in FIG. 4, the first end 14A of the fiber bundle 14A is fused into a substantially circular shape while the second end 14B of the fiber bundle 14 is fused into a substantially rectangular shape to approach the shape of a linear slit for the input interface 83. The individual junction fibers 15 can be loose in between their respective ends or continuously fused along the length thereof. Care must be exercised to maintain the same approximate surface area on each end of the fiber bundles 14A and 14B so that the numerical aperture of this fused, round-to-slit adapter is not altered inadvertently.

In the embodiment illustrated in FIG. 4, each junction fiber 15 has a diameter d4 that is less than diameter d2 of each collection wave guide 70 and also less than diameter D1 of the mixing and transmitting device 12. The stabilized light S transmitted through the junction optical wave guides 15, which have a smaller diameter d4 relative to diameter D1 of the mixing and transmitting device 12, increases the spatial resolution of the light energy propagating therethrough.

The size of the junction fibers 15 is selected such that the fibers 15 can be readily spread to form a linear array, as shown by the fused end region of the second end 14B. The diameters of the junction optical wave guides 15 of the exemplary embodiment are also selected to propagate light up to at least a 6 wave number resolution, where "wave number" is the number of waves per centimeter of light of a given wavelength. Further, the diameter d4 of the junction wave guides 15 is selected such that the numerical aperture of the linear array 14B is matched to the light acceptance characteristics of the light processing unit 80. In the exemplary embodiment, the light processing unit is a "fast" spectrograph that can accept a high numerical aperture fiber of 0.22, 0.28 or 0.34 or greater.

A "fast" spectrograph refers to the ability of the spectrograph to accept input light at a greater incident angle compared to a "slower" spectrograph that accepts light at a lower incident angle. The wider the angle of incident light that a spectrograph can collect, the "faster" the spectrograph. For example, a spectrograph having an f-number of f/4 is slower than a spectrograph having an f-number of f/2.

The shapes of the fused first and second ends 14A and 14B of junction fiber bundle 14 and the relative sizes of the individual junction fibers 15 are not limited to the shapes and sizes illustrated in FIG. 4. The shape of the fused ends 14A and 14B and the respective diameters d4 of the individual junction fibers 15 are chosen to appropriately match to the input aperture 83. The combined light R-S has a substantially uniform intensity at the output where the differences of light intensities originating from the collection wave guides 70 are substantially reduced or eliminated. The stabilized light S then propagates along the junction feed wave guides 15 into the linear or slit input of the light processing unit 80.

Figure 5A:
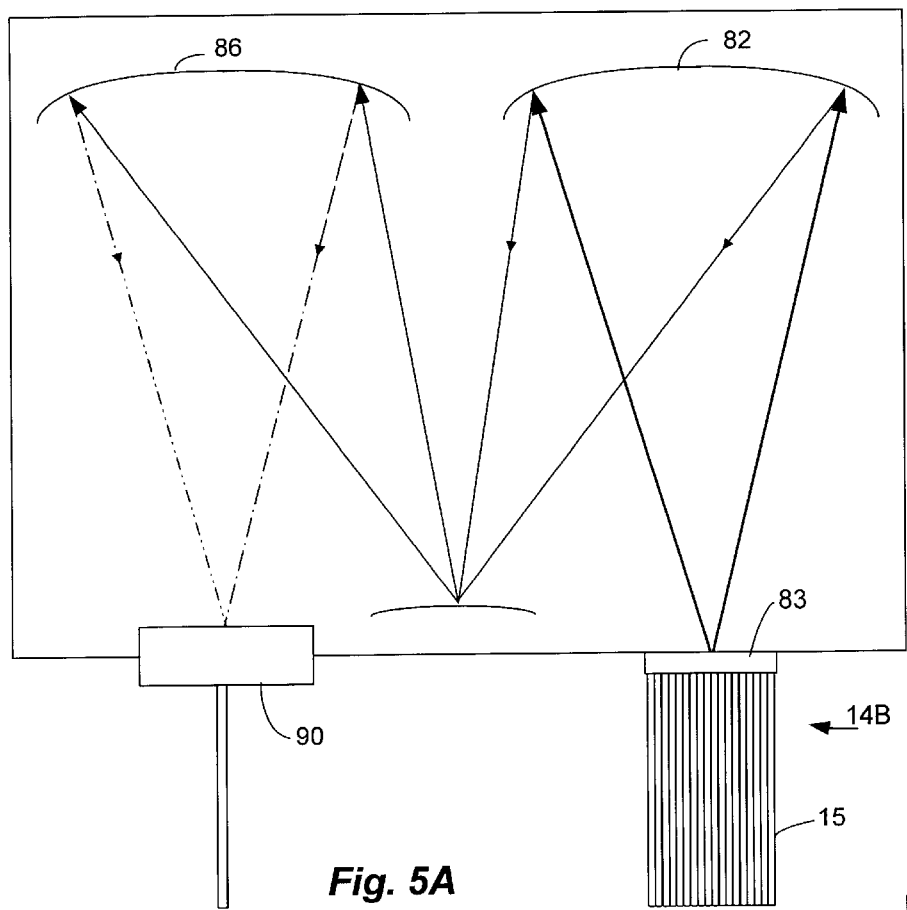
FIG. 5A is a diagram that illustrates an exemplary light processing unit as set forth in the system diagram of FIG. 1.

As illustrated in FIG. 5A, the second fused end 14B of the junction fiber bundle 14 is linked to the light processing unit 80. The light processing unit 80 is typically a dispersive light instrument such as a wave length separator unit that is designed to analyze a spectral distribution of electromagnetic energy including reflected laser light. Wavelength separator units are commonly referred to as spectrographs. Exemplary spectrographs are available from the following vendors: Acton Research Corporation of Acton, Mo.; Renishaw PLC of Gloucestershire, United Kingdom; Detection Limited Inc. of Laramie, Wyo.; Kaiser Optical Systems of Anne Arbor, Mich.; and Process Instruments of Salt Lake City, Utah.

The stabilized light S exits the individual junction wave guides 15 and enters into the light processing unit 80 through an input aperture 83 such as a rectangular slit. The stabilized light S is reflected off of a concave mirror 82 onto a detraction grating 84. The defraction grating 84 sets up an interference pattern. For the exemplary embodiment, the defraction grating 84 can be a ruled-type grating or a volume holographic grating. The stabilized light S dispersed off the grating is separated into different wave lengths. This dispersed and separated light is then reflected from another concave mirror 86 and focused onto an optical-to-electrical converter 90. Multiple light rays or images are focused on the optical-to-electrical converter 90, where each image is spread at different wave lengths. In the exemplary embodiment, the optical-to-electrical converter 90 can be a charge coupled device (CCD) camera.

Vendors for exemplary CCD cameras include the following: Roper Scientific of Georgia and Princeton Instruments of Trenton, N.J. The CCD camera is preferably a near-infrared (NIR)-enhanced chip device for operation above 800 nanometers to process laser light-type excitations. To optimize operation of the CCD, it can be cooled to a temperature range of about −50° celsius to −70° celsius. Cooling of the CCD can be accomplished with liquid nitrogen or other electromechanical cooling mechanisms. Such cooling of the CCD reduces noise and hence, increases efficiency of the detection of elastic scattering of photons of the emitted light. Efficiency is also increased when the CCD size is matched to the height of the linear array of junction fibers 15.

To further optimize the operation of the CCD, aberrations or image curvature that causes the light ouput of the linear array of fibers or shaped end at the input interface 83 of the light processing unit 80 to be imaged with some curvature on the CCD should be corrected. Such aberrations can be corrected by using high resolution optics or through making such corrections with light processing software.

The spectrograph in the exemplary embodiment is rigid so as to substantially reduce the possibility of changing the optical configurations thereof. Further, the spectrograph in the exemplary embodiment does not have any moving parts.

Figure 5B:
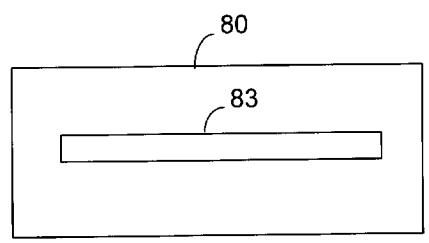
FIG. 5B is a diagram that illustrates an exemplary input aperture for the light processing unit shown in FIG. 5A.

As illustrated in FIG. 5B, the light processing unit 80 can include an input interface 83 that is shaped into a rectangular slit. However, other shapes of the input interface 83 are not beyond the scope of the present invention. The shape of the input interface 83 in the exemplary embodiment is selected in order to maximize wave length separation efficiency of the light processing unit 80.

Figure 6:
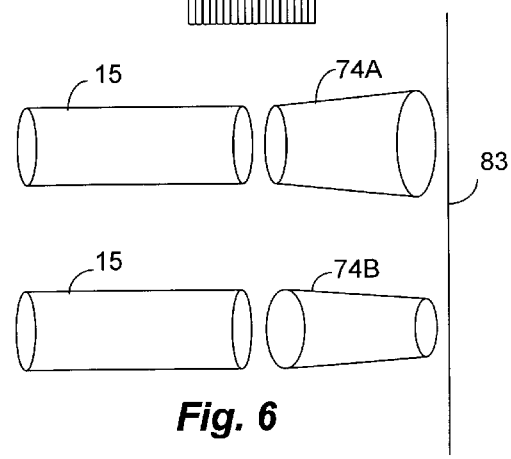
FIG. 6 is a diagram that illustrates adaptation details for individual wave guides of the light stabilizing interface shown in FIG. 4.

FIG. 6 illustrates first and second adaptation devices 74A and 74B that are designed to connect junction fibers 15 to the input interface 83 of the light processing unit 80. With these designs, the light flux density of each junction fiber 15 is maximized at the input interface 83. The first and second adaptation devices 74A and 74B are typically optical wave guides that have a substantially frustum shape. The frustum shaped wave guides 74A and 74B are generally used at input interfaces 83 where light angle manipulation or f-number manipulation is required. Therefore, if a lower f-number component needs to be matched to a higher f-number component, then an uptapered (increasing cross-sectional area relative to junction fiber 15) frustum such as adaptation device 74A is utilized. Similarly, if a higher f-number component needs to be matched to a lower f-number component, then a down-taper (decreasing cross-sectional area relative to junction fiber 15) optical wave guide frustum, such as adaptation device 74B, is utilized.

The f-number of a lens or other optical interface, such as the input interface 83, is defined as follows:

$$f\text{-number} = efl/D$$

The variable "efl" is the lens effective focal length and "D" is the diameter of an entrance pupil. The relationship between the f-number and a numerical aperture (NA) is defined as follows:

$$f\text{-number} = 1/2(NA)$$

In order to match numerical apertures between a lens system and an optical fiber, the relationship between the effective focal length, entrance pupil diameter and numerical aperture are as follows:

$$efl/D = 1/2(NA)$$

or $$NA = D/2(efl).$$

For an optical wave guide such as an optical fiber, a numerical aperture is equal to the square root of a difference between the squares of the refractive indices of the core and surrounding cladding.

FIG. 7 is a ray-tracing sketch that generally illustrates the combining and stabilizing function of the mixing and transmitting device 12 for the stabilizing interface 10. The reflected light R propagating along the collection optical wave guide 70 moves into the mixing and transmitting device 12, which combines, substantially stabilizes, and evenly distributes the reflected light R into the junction wave guides 15. The substantially stabilized light S then propagates through the junction wave guides 15 to the input interface 83. While the ray tracing depicted in FIG. 7 may show an angular change of the rays propagating within the mixing and transmitting device 12, in the exemplary embodiment, there is no angular change of the rays in the mixing and transmitting device 12.

FIG. 8 illustrates a second exemplary embodiment of the light stabilizing interface 10'. In this second embodiment, a mixing and transmitting device 12 of the first embodiment (not shown) is modified to form the light stabilizing interface 10'. Specifically, a mixing and transmitting device 12

(not shown) is heated and compressed to form a collection wave guide matching section 12' and a transition region 22 that terminates in a shaped end region 24. The shaped end region 24 is designed to substantially match to the geometry of the input interface 83. In the embodiment illustrated in FIG. 8, the shaped end region 24 has a substantially rectangular shape to match to the substantially rectangular shape of the input interface 83. The total surface area of the transition region 22 in this embodiment is designed to remain constant relative to the collection wave guide matching section 12'.

To accomplish the goal of maintaining a constant total surface area between the transition region 22 and collection wave guide matching region 12', a dye is fabricated from material that will withstand temperatures at which the mixing and transmitting device 12' prime will soften. The dye should have an interrectangular cavity (not shown) of the desired dimensions. Typically the dye needs a thin rectangular cross-section. The dye has a top and a bottom half (not shown) which meet together. The dye (not shown) and the mixing and transmitting device 12 are heated in unison, and the dye is compressed to closure. As the dye is compressed, the mixing and transmitting device 12 in the transition region 22 takes on the shape of the desired rectangular cross-section.

Ideally, the transition from circular cross-section to rectangular is accomplished gradually along the light stabilizing interface's 10' longitudinal access. The light stabilizing interface 10' of FIG. 8 can have substantially less light energy loss relative to the first embodiment illustrated in FIG. 4 due to the relative fewer number of interfaces. However, the linear array of optical wave guides 15 for the first embodiment illustrated in FIG. 4 is currently easier to manufacture but has an associated coupling loss due to the interstitial spaces between junction optical wave guides 15.

Stabilizing Reflected Light Process

Figure 9:
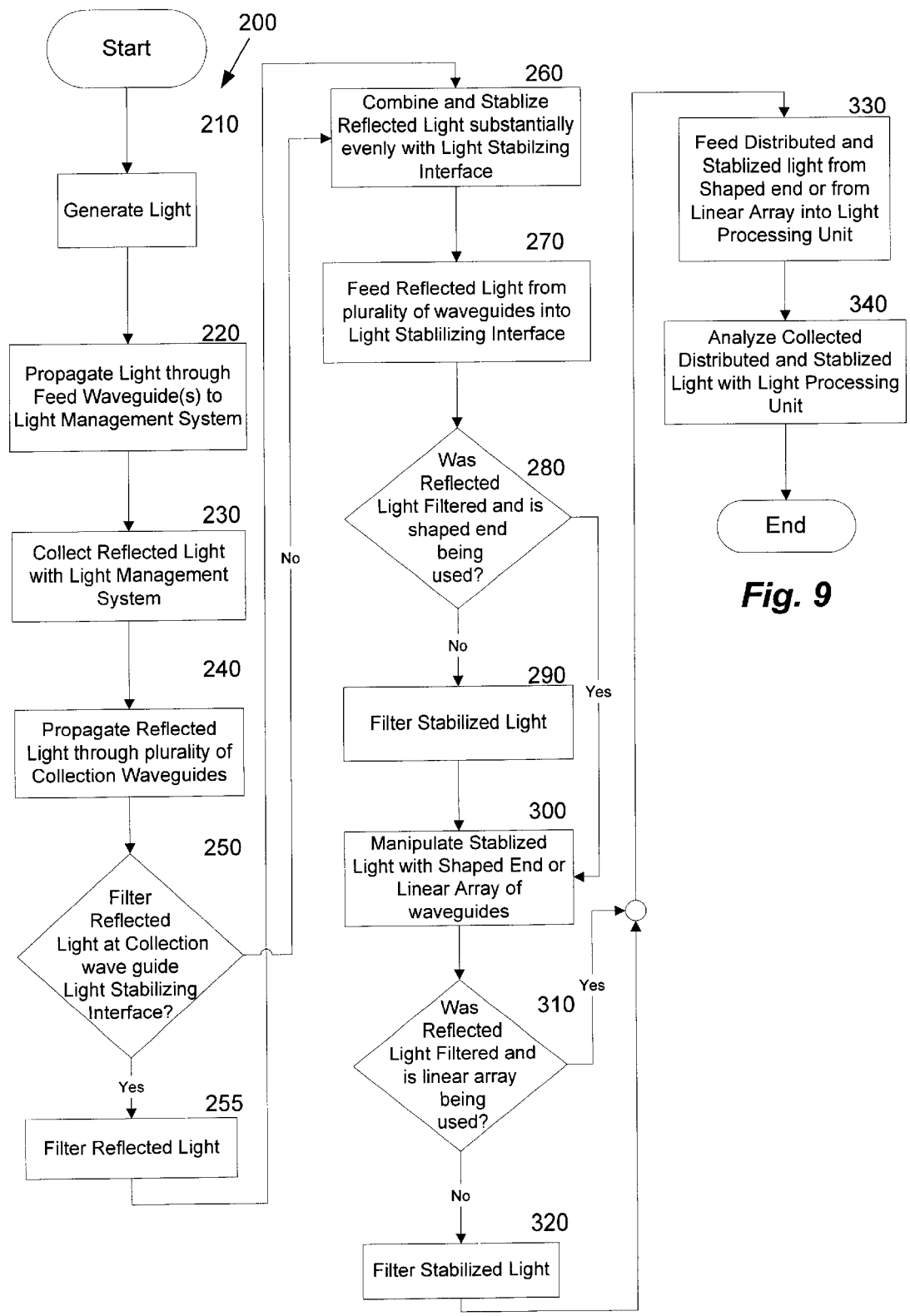
FIG. 9 is a logic flow diagram illustrating a process for stabilizing reflected light in accordance with an exemplary embodiment of the present invention.

FIG. 9 is a logic flow diagram of a process 200 for stabilizing reflected light. Process 200 begins in step 210 in which light is generated with a light source unit 50. In step 220, the source light is propagated through one or more optical wave guides to a light management system 30.

In step 230, the light management system unit 30 collects reflected light. In step 240, the light management system unit 30 propagates the reflected light through the collection wave guides 70. In step 250, it is determined whether the reflected light R should be filtered prior to exiting the collecting wave guides 70. If the answer to the inquiry of decision step 250 is negative, the "No" branch is followed to step 260. If the answer to decision step 250 is positive, the "Yes" branch is followed to step 255 where the reflected light R is filtered.

In step 260, the reflected light R is fed into the light stabilizing interface 10. In step 270, the light stabilizing interface 10 combines and stabilizes the light intensity of the reflected R light in a substantially even manner. In step 280, it is determined whether the reflected light R was filtered in previous step 250, prior to the reflected light's R entry into the light stabilizing interface 10 and if a shaped end is being used. If the answer to the inquiry of decision step 300 is negative, the "No" branch is followed to step 290. If the answer to decision step 280 is positive, the "Yes" branch is followed to step 300. In step 290, the stabilized light R-S is then filtered before it enters the input interface 83.

In step 300, the propagation path of the stabilized light R-S is manipulated with either a shaped end or a linear array of junction wave guides 15. In step 310, it is determined whether the reflected light R was filtered in previous step 250, prior to the reflected light's R entry into the light stabilizing interface 10, and if a linear array is being used. If the answer to the inquiry of decision step 310 is negative, the "No" branch is followed to step 320. If the answer to decision step 310 is positive, the "Yes" branch is followed to step 330. In step 320, the stabilized light R-S is filtered before it enters the input interface 83. While filtering of the reflected light can occur at either end of the light stabilizing interface, it is not beyond the scope of the present invention to filter the reflected light at both sides of the light stabilizing interface.

In step 330, the stabilized light S is fed from the shaped end or from the linear ray into the light processing unit 80. In step 340, the stabilized light S is analyzed.

Exemplary Biological Testing and Treatment Environment

The inventive technologies for stabilizing reflected light is appropriate for medical treatment and drug development. The present system can provide enhanced capabilities for in vivo (in body) analysis of the chemical makeup of living tissue and materials interacting therewith. When using Raman spectroscopy techniques, the inventive method and system control light based interactions and provide measurements that yield unexpectedly precise information. Prior to the present invention, Raman spectroscopy had a reputation of great potential, but that potential was largely unrealized because of technology difficulties. The present invention for stabilizing reflected light can yield surprisingly effective applications of Raman spectroscopy.

Real-Time, in-vivo Chemical Window for Combinatorial Chemistry Testing

The method and system for stabilizing reflected light can provide, for the first time, a high-clarity, real-time, in vivo chemical window into the mechanisms of drug-tissue interactions. The present invention can address many issues and needs associated with clinical pharmacology: Drug input and disposition (drug absorption, bioavailability, drug distribution, drug elimination—both metabolism and excretion); kinetic principles of drug administration (basic pharmacokinetic parameters, drug administration, variability in parameter values); monitoring drug treatment (monitoring responses, monitoring drug in plasma—including indications for monitoring, complicating factors, the therapeutic window, evaluation of a measured concentration, and frequency in monitoring); pharmacodynamics (mechanisms of drug action—including membrane interaction, receptor interaction, and chemical interaction and dose-response relationships); factors affecting drug response (pharmacogenetics, drug interactions—including pharmacodynamic interactions, pharmacokinetic interactions, and principles of management); drug toxicity (preclinical and clinical evaluation of toxicity, adverse drug reactions, carcinogenesis, benefit-to-risk ratio); patient compliance; neurotransmission; prostaglandins, thromboxanes, and leukotrienes (biologic actions and potential therapeutic applications); and calcium antagonists.

The inventive method and system for stabilizing reflected light solve a fundamental problem with drugs, drug usage, and drug development as related to ambiguity associated with drug effects. The method and system's ability to provide solutions to such complex problems relates to its unexpectedly high performance and fidelity in discriminating subtle differences in chemical composition.

Further, the present invention provides an exemplary method of developing drug-based treatment that includes compiling a set of compounds that are likely to influence a desired therapeutic outcome. The method includes mapping Raman spectral features of tissue to a health condition, and introducing at least one compound from the set of compounds into at least one living organism. Next, informative Raman spectra is observed from living tissue of the organism with the system set forth in FIG. 1. The compound efficacy is then evaluated by inferring changes in the health condition from spectral changes noted in the output produced by the computing unit 120. In one aspect of the invention, the tissue responds over time to at least one of the introduced compounds and Raman spectra are observed at intervals corresponding to a predicted time response of the treatment. In another aspect of the invention, the set of compounds is produced by combinatorial chemistry. In an additional aspect, the set of compounds is compiled by genetic factors.

The present invention also provides an exemplary method for assessing medical treatment efficacy by introducing a chemical into a living vertebrate and recording useful Raman spectra from living tissue of the vertebrate. Then, tissue response to the chemical can be inferred by noting changes in the Raman spectra.

Exemplary Implementation: Monitoring Experimental Clinical Drug Trials

Opposite to the outcome-based approach of the conventional art, the method and system for stabilizing reflected light offer a biochemical window into the mechanisms of the drug's interaction with the tissue. For example, the method and system allows the scalp of a patient in a baldness study to be investigated while the biochemistry changes and variation within the test group are analyzed. It is operable with extreme fidelity due to unexpectedly high performance.

To illustrate how the present invention transcends the drug development cycle, assume that 10% effectiveness was the maximum that could be achieved. Further assume that the 10% innately exhibit a specific chemical marker that correlates to treatment efficacy. The marker could be due to environmental or genetic influence or some combination thereof In this circumstance, the method and system for stabilizing reflected light is a powerful tool that can guide treatment. The present invention can be used to test patients seeking a cure for baldness; if the marker is present, the method and system for stabilizing reflected light can guide a physician to administer the drug. In this manner, a drug that is not suited for commercialization due to its poor performance on the general population may become a commercial success. The baldness example is generalized to the entire skin system such that the present invention is effective on across the range of dermatological disorders and related afflictions.

With beam steering of the present invention, the ability to selectively investigate various depths of the skin organ system is realized. This is important as many diseases, conditions and or important chemicals are localized in depth. Likewise, many treatments must penetrate and/or act at selective depths. Various treatments include ointments, creams, lotions, and solutions. Representative topical steroid products include hydrocortisone acetate, desonide, flurandrenolide, desoximetasone, betamethasone dipropionate, halcinonide, and diflorasone diacetate. The present invention can be used to analyze the influence of these types of materials.

Figure 3:
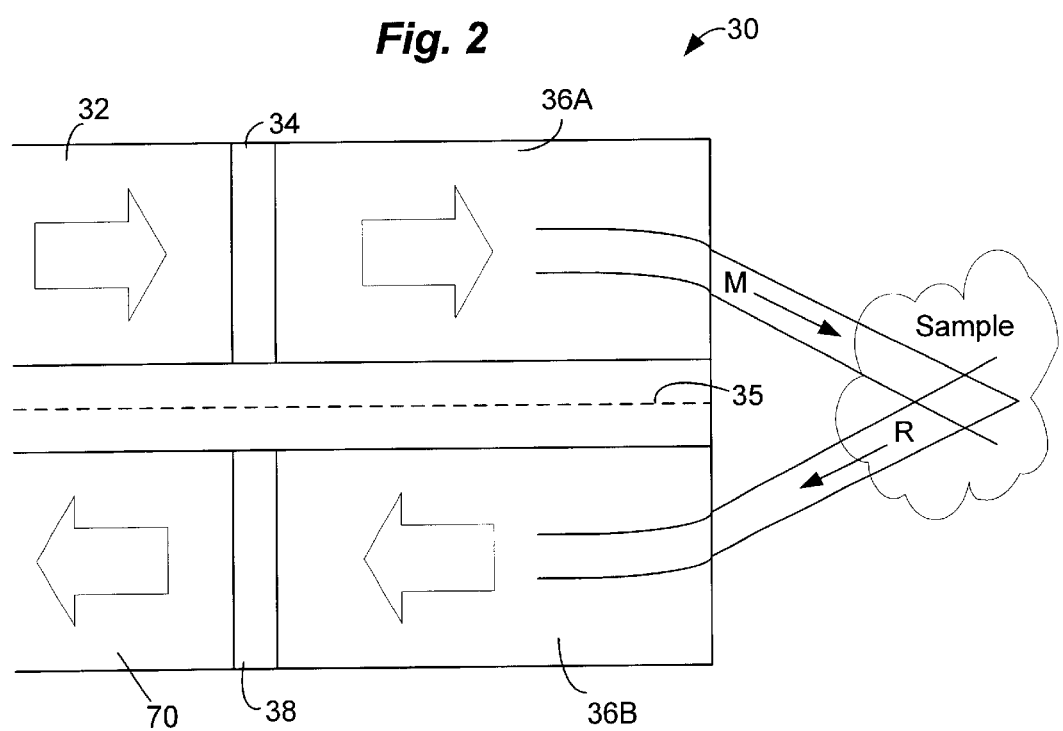
FIG. 3 illustrates an exemplary light management system unit as set forth in the system diagram of FIG. 1.

Specifically, the present invention provides an exemplary method for determining the presence of at least one chemical moiety in living tissue. First, a light spectrum of the tissue or sample 40 is created by the following subprocess: Exposing the tissue 40 to Raman-energy in the form of light M with the light management system 30 as illustrated in FIG. 3. The reflected light R is fed to the light stabilizing interface 10, as illustrated in FIG. 1, where it is combined, stabilized and distributed evenly. The stabilized light S is then fed into the light processing unit 80 where the light is separated into its respective wavelengths. This wavelength information is then sent to the optical-to-electrical converter 90. The computing unit 120 later analyzes the digital wavelength data and produces the tissue spectrum.

Secondly, the spectrum of the tissue is then compared to the Raman spectrum of a known which includes the chemical moiety in a comparable environment. Alternatively, the spectrum of the tissue can be compared to a known which includes the chemical moiety in known amounts in a comparable environment. From the first comparison of a known Raman spectrum, it can be determined whether the spectrographic peaks of the chemical moiety are present in the resultant tissue spectrum. From the second comparison of the chemical moiety in known amounts, the peak intensities of the tissue as compared to the spectrographic peaks of the spectrum of the known spectrum can be measured.

In one aspect of the invention, the chemical moiety is a part of the living tissue. In another aspect, the moiety can be artificially introduced into tissue to interact with at least a part of the tissue, such as in the application of chemicals in the baldness study. In the baldness study and in other aspects of the invention, the chemical moiety that is studied can be subcutaneous (beneath the skin). Besides topical studies, the light management system 30 can be partially submersed in blood or used to analyze plaque tissues without removal from the organism.

In a further aspect, the present invention provides an exemplary method of evaluating the interaction of a drug with the tissue of a vertebrate by introducing a drug into an organism 40 and then generating monochromatic light M with the light source unit 50. In an additional aspect of the method for evaluating drug interaction, the monochromatic light M passes through a monochromatic enhancer 34 to increase the purity of the light M and reduce any fiber optic based interference.

Next, the monochromatic light M is carried into the organism 40. The light management system 30 then tracks Raman light-matter interactions within the organism 40. The light management system 30 segregates the signal of the Raman light-matter interactions or reflected light R from the signal of the highly monochromatic light M.

Subsequently, the light management system 30 carries the Raman light-matter interaction signal or reflected light R out of the organism while minimizing interference by utilizing filters 16. After the reflected light R is combined, stabilized, and distributed evenly in the light stabilizing interface 10, the light processing unit 80 separates the stabilized light S into constituents or wavelengths wherein the constituents correlate with energy-levels of the Raman light-matter interactions. The computing unit 180 then records the frequency of occurrence of the light-matter interactions at multiple energy-levels to generating a Raman spectrum. Next, the acquired Raman spectra is inspected for features attributable to the drug introduction into the organism 40. And lastly, from these results drug interaction can be inferred.

Cancer Research

As another example, assume a new treatment is devised to combat breast cancer tumors and that the treatment is a pharmacological agent administered intravenously to the patient. A clinical study may be organized on patients with inoperable breast cancer tumors. The tumor sizes of the patients may be measured during the study and success gauged on the treatment's effectiveness in shrinking tumors. The present invention can be used to monitor the drug's interaction with the tumor at the biochemical level. It is possible due to the unexpectedly high performance of the method and system for stabilizing reflected light.

For example, high metabolic activity correlates with growth rate. Biochemicals such as metabolites within the tumor are associated with tumor expansion. The light management system of the present invention, tipped with a needle, can assess not only the metabolites but also the drug uptake and even search for unknown, unexpected chemical interactions. The needle can be inserted into the tumors with minimal invasion. Again, the present invention can provide significant benefits beyond the drug development utility. With breast malignant tumors, as with other cancers, some tumors respond favorably to some treatments; and, there are many treatments available to the physician. There is currently not an effective method to match a tumor to treatment.

However, the method and system for stabilizing reflected light can map the biochemical aspects of a specific tumor in a specific patient to treatment types historically successful on tumors with correlating biochemical aspects. Such a treatment may entail a cocktail of chemicals, surgery, radiation, diet, therapy, and other interventions.

The present invention provides an exemplary method of mapping the biochemical parameters of disease. This exemplary method includes recording informative Raman spectra from within a living organism. To produce the Raman spectra, monochromatic light M is initially carried into with the light management system 30. Reflected light R is then carried out of the living organism with the light management system 30 The reflected light R is combined, stabilized, and distributed evenly with the light stabilizing interface 10. Next, the stabilized light S is separated into wavelengths in the light processing unit 80. Later, the computing unit 120 generates a Raman spectra of the illuminated part of the organism.

Subsequently, the disease state can be evaluated by conventional means such as X-rays, MRIs, etc. Then, the Raman spectra can be correlated with the disease state. In a further aspect, the Raman spectra can be correlated with Raman signatures of known chemical standards.

Monitoring Eye Disorders

As another example, consider treatments for disorders of the eye such as cataracts, scleritis, uveitis, vascular retinopathy, macular degeneration, retinitis pigmentosa, glaucoma, optic neuritis, and optic atrophy. Many eye disorders progress slowly, even over many years or decades. A potential pharmacological treatment might be deemed effective if it could be administered in the early phases of disorder onset and slow or halt disease progression. Factors hindering the assessment of a candidate treatment's effectiveness include the slow progress of many eye disorders, the negative aspects of extracting biopsy's from critical eye tissue, and the subjective nature of evaluating disease progression. Thus, a study of treatment efficacy might take many decades using current methodology and tools. However, the present invention has the ability to detect the biochemical basis of the disease to provide immediate, quantitative feedback. For example, cataracts are developmental or degenerative opacities of the lens. The extent of disease progression can be quantified with the light management system 30 when it is tipped with a means to project test signals into and record measurement signals out of a lens. Since opacity results from chemical changes within the material of the lens, treatment efficacy can be gauged rapidly. In this manner, the inventive method and system can provide a closed loop feedback to the drug development process. The effectiveness of treatment candidate materials such as antioxidants, catalase, superoxide dismutase, vitamin E, aminoguanidine can be readily assessed.

Monitoring Time Release of Ingested Drugs

As another example, a drug may be ingested in table or capsule form. As the capsule dissolves, the drug is released for uptake by the body. Significant ambiguity surrounds the time release solubility of the medication. The light management system 30, when tipped with a thin flexible implement, aids the development and analysis of the appropriate release structure for the medication. The flexible implement (attached to analytical hardware, such as the computing unit 120 on an opposing end) can be swallowed so that the dissolution, interaction with gastric fluids, and uptake by tissues in the gut is monitored in real-time.

Specifically, the present invention provides an exemplary method for determining the impact on living tissue of artificially introduced constituents in animal body fluids. First, tissue is selected to be analyzed and then a chemical is introduced into the tissue. Then Raman spectroscopy is implemented with the reflected light stabilizing system, as illustrated in FIG. 1, to determine the extent of change in a selected chemical characteristic.

Monitoring Brain Diseases

As another example, drug therapies to treat Alzheimer's disease have been difficult to develop. This is due to the inability to monitor the progression of the disease at a biochemical level. As with the eye, the brain is an organ from which biopsies are not readily extracted. Even if biopsies could be taken, the critical biochemical markers may be transitory so that they do not survive the time delay between removal and assay. The present invention can provide analysis without tissue removal so that multiple drug candidates are readily tested.

Monitoring Heart Diseases

Atherosclerosis and arteriosclerosis are complex medical conditions that are the subject of significant global efforts in medical research. The magnitude of the research is evidence of the lack of understanding of the disease, its causes, progression, treatment, etc. Factors that contribute to the research difficulty include difficulty in extracting biopsies of the key tissues, lack of assays to analyze the tissue in vivo, and the slow onset and progression of the disease. Instances have been reported in which drugs were given to patients with severe blockages. The patients were evaluated as being at a high risk of heart attack because of the reduced blood flow associated with the blockages. The drugs were found effective in reducing the rate of heart attack. However, the blockage reduction resulting from the drugs was insufficient to explain the reduced heart attack rate. Current theory suggests that certain lesions, so called vulnerable plaque, are prone to rupture. The rupture results in a life-threatening cascade of events. However, without an in vivo method and system to definitively analyze the plaque, understanding the drug interactions with tissue is speculative.

The inventive method and system for reflected light stabilization can provide in vivo, quantitative biochemical composition ideally suited to the task. Consequently, the present invention can assess incremental changes in disease progression, even in the early stages of disease onset. This facilitates the development of prophylactic drugs, nutritive additives, dietary supplements, and foods that would reduce disease onset and/or minimize disease evolution.

To study the mechanisms of atherosclerosis and its response to various therapies, a group of subjects with various stages of the disease can be assembled. Candidate compounds include those already approved for related, or non-related, treatments. The compounds can also be derived from gene-based drug development or combinatory chemistry techniques. Also, the drugs can be selected from those already in use but for which their effects are not well understood and their use is not optimized. Candidate compounds, include anti-oxidants, vitamins, vitamin A, vitamin E, antibiotics, aspirin, lipid lowering agents (resins (cholestyramine, colestipol), fibrates (gemfibrozil, fenofibrate), niacin, statins (HMG-CoA reductase inhibitors, fluvastatin, lovastatin, simvastatin, pravastatin, atorvastatin, and cervastatin), roxithromycin, azithromycin, dexamethasone, matrix-degrading metalloproteinases, angiotensin converting enzyme inhibitors such as captopril, enalapril, fosinopril, lisinopril, and ramipril, and acyl-coenzyme A cholesterol acyltransferase inhibitors. The drugs can be administered individually or as a cocktail with additive influence. Other therapies include stents, stents with embedded compounds, low temperature therapies, photodynamic therapy (light-activated compounds), two-photon (non-linear) photo-dynamic therapy, laser ablation, diet, and lowering tissue temperatures.

To initiate the study, the stage of the disease can be ascertained in each subject. A segment of the group would be given placebos, another segment can be given medications thought likely to produce a positive therapeutic effect. The desired effect can be lesion stabilization, blockage reduction, change in lesion composition, reduced clot in lesions that rupture, etc. Periodically, the subjects could be inspected with the present invention to assess the disease state.

Beyond gauging disease progression, the inventive method and system for stablizing reflected light can reveal subtle changes in the biochemical aspects of the interactions between disease, drug, treatment, and tissues. A thin, flexible catheter tip facilitates insertion into vascular lumens. Chemical composition of vascular tissue is spatially mapped lengthwise, and depth-wise, as appropriate. Individual lesions can be closely inspected. The study data can also be used to map treatments to patient conditions such that optimal treatments could be prescribed for patient case.

Although Raman spectroscopy has been suggested as a candidate analytical technique for biomedical analysis, extensive experimentation by many of the world's leading research organizations has met fundamental roadblocks. A Raman spectrum contains a wealth of information so it is not surprising that thousands of uses have been contemplated for this spectrographic technique. Systems and methods have neither been available to extract meaningful Raman spectra from living tissue nor provide in vivo analysis based on Raman light-matter interactions. No means have been available to provide high specificity quantitative analysis of in vivo tissue.

However, the present invention can extract high quality Raman spectra from living tissue to provide non-destructive, quantitative and qualitative chemical analyses of biological materials. As evidenced by the aforementioned examples, the inventive technology for stabilizing reflected light can be useful for drug and therapy development as well as many other uses.

One of the attributes to the results rendered possible by the present invention is believed to be the high degree of monochromacity of the Raman excitation light that is delivered to the tissue and the characteristic of precluding chromatic degradation during transport. Another is believed to be the finesse of the segregation of excitation and Raman scattered tissue light of the present invention. Another is believed to be the efficiency of the transfer of light between the carrying apparatus and the tissue. Further, another is believed to be the efficiency of the transfer of the light between the carrying apparatus and the detection unit. Another is believed to be suppression of interference. Another is believed to be beam steering of the present invention. Another is believed to be high performance filtering. Another is believed to be minimizing the number of components and air interfaces in the optical pathways. Another is believed to be means of the present invention for imparting instrumentation with selective sensitivity to the specific light-matter interactions of interest. Another is believed to be means of the present invention for imparting instrumentation with selective sensitivity to specific regions of tissue. Another is believed to be the ability to operate in a blood environment. Another is believed to be an integrated optics approach.

From the foregoing description, it will be appreciated that the present invention provides a light stabilizing interface linked to a collection wave guides for combining and stabilizing reflected light into a substantially even spatial distribution of light energy with a substantially uniform light intensity. Even spatial distribution and uniform intensity of reflected light energy are desirable qualities and enhance light measurement techniques such as Ramon spectroscopy.

In one aspect of the invention, the stabilization and substantially even spatial distribution of reflected light is accomplished by a mixing and transmitting device comprising a single optical fiber and optical junction wave guides in the form of optical fibers having a smaller diameter relative to the mixing and transmitting device. The optical junction wave guides are shaped into a linear array in order to maximize the light fed into an input interface of a light processing unit that has a predefined geometrical configuration (usually a slit).

For another aspect of the present invention, the stabilization and substantially even spatial distribution of reflected light is accomplished by a single, integral device that includes a collection wave guide matching section and a transition region. The transition region terminates in a shaped end region that is designed to substantially match the geometry of the input interface of the light processing unit. For example, the shaped end region has a substantially rectangular shape to match to the substantially rectangular shape of the input interface.

In another aspect of the present invention, the method and system for stabilizing reflected light enhances the drug development process by providing real-time in-vivo chemical analysis of the interactions between drugs and living tissue. Specifically, the method and system enable accurate detection of chemical composition and quantity in living tissue.

While the present invention is typically employed in a biomedical environment as set forth in the illustrative embodiments and exemplary implementations, the invention is not limited to these applications and can be used in other areas that require light stabilization in an optical fiber environment.

For example, the present invention may be employed in the communications field. Specifically, in the Cable TV or telecommunications fields which employ optical fibers, the method and system for stabilizing reflected light could be used to evaluate the efficiency of light propagation along a fiber optic network. Further, the light stabilizing interface itself could be used at nodes or junctions along a fiber optic communications network.

From the foregoing, it is apparent that the present invention has been described in relation to particular embodiments which are intended in all respects to be illustrative rather than restrictive. Alternative embodiments will become apparent to those skilled in the art to which the present invention pertains without departing from its spirit and scope. Accordingly, the scope of the present invention is defined by the appended claims rather than the foregoing description.

What is claimed is:

1. A reflected light stabilizing system comprising:

a light source unit for generating light;

a plurality of optical feed wave guides operatively linked to said light source for propagating the light in a first direction;

a light management system operatively linked to said plurality of optical feed wave guides for accepting light in said first direction and outputting said light to a sample, said light management system further operative to collect light reflected from the sample;

a plurality of optical collection wave guides for collecting the reflected light from the light management system propagating in a second direction;

a light stabilizing interface operatively linked to said plurality of collection wave guides for combining and stabilizing the reflected light into a substantially even spatial distribution of light energy with a substantially uniform light intensity; and a light processing unit operatively linked to said light stabilizing interface for processing the light energy.

2. The system of claim 1, further comprising a plurality of optical connection wave guides disposed between said light stabilizing interface and the light processing unit.

3. The system of claim 2, wherein the plurality of optical connection wave guides are arranged into a substantially linear array.

4. The system of claim 1, wherein said light stabilizing interface includes a shaped end which is operatively linked to said light processing unit.

5. The system of claim 4, wherein the shaped end of the light stabilizing interface has a polygonal shape.

6. The system of claim 5, wherein the shaped end of the light stabilizing interface is substantially rectilinear.

7. The system of claim 1, wherein the light processing unit is an instrument that disperses the light energy.

8. The system of claim 1, wherein the light processing unit includes a wavelength separator unit.

9. The system of claim 8, wherein the light processing unit is a spectrograph.

10. The system of claim 1, further comprising a filter disposed between said optical collection wave guides and said light stabilizing interface.

11. The system of claim 1, further comprising a filter disposed between the optical feed wave guides and said light stabilizing interface.

12. The system of claim 1, wherein the light stabilizing interface comprises a single optical wave guide.

13. The system of claim 12, wherein the single optical wave guide is an optical fiber having a first diameter and each feed wave guide has a second diameter, said first diameter is substantially larger than said second diameter.

14. The system of claim 12, wherein said single optical wave guide has a substantially cylindrical shape.

15. A method for creating a substantially even spatial distribution of reflected light energy, comprising the steps of:

generating light with a light source unit;

propagating the light through a plurality of optical feed wave guides to a light management system;

outputting light to a sample;

collecting reflected light with the light management system;

collecting the reflected light from the light management system with a plurality of optical collection wave guides;

feeding the collected reflected light from the optical collection wave guides into a light stabilizing interface;

stabilizing and combining the reflected light into a substantially even spatial distribution of light energy with a substantially uniform light intensity with the light stabilizing interface; and feeding the distributed light energy from the light stabilizing interface into a light processing unit.

16. The method of claim 15, further comprising the step of feeding the distributed light energy from the light stabilizing interface into a plurality of optical wave guides operatively linked to the light processing unit.

17. The method of claim 16, further comprising the step of arranging the plurality of optical wave guides operatively linked to the light processing unit into a substantially linear array.

18. The method of claim 15, further comprising the step of feeding the distributed light energy from a shaped end of the light stabilizing interface into a light processing unit.

19. The method of claim 18, wherein the shaped end of the light stabilizing interface has a polygonal shape.

20. The method of claim 18, wherein the shaped end of the light stabilizing interface is substantially rectilinear.

21. The method of claim 15, wherein the light processing unit is an instrument that disperses the light energy.

22. The method of claim 15, wherein the light processing unit includes a wavelength separator unit.

23. The method of claim 22, wherein the light processing unit is a spectrograph.

24. The method of claim 15, further comprising the step of filtering one of the reflected light and distributed light energy.

25. The method of claim 15, wherein the light stabilizing interface comprises a single optical wave guide.

26. The method of claim 25, wherein the single optical wave guide is an optical fiber having a first diameter and each feed wave guide has a second diameter, said first diameter is substantially larger than said second diameter.

* * * * *